United States Patent
Yu et al.

(10) Patent No.: US 10,457,993 B2
(45) Date of Patent: Oct. 29, 2019

(54) BIOMARKER RNF6 FOR COLORECTAL CANCER

(71) Applicant: The Chinese University of Hong Kong, Shatin (CN)

(72) Inventors: Jun Yu, Shatin N. T. (CN); Joseph Jao Yiu Sung, Ma on Shan (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 185 days.

(21) Appl. No.: 15/085,790

(22) Filed: Mar. 30, 2016

(65) Prior Publication Data
US 2017/0283876 A1  Oct. 5, 2017

(51) Int. Cl.
*C12Q 1/68*  (2018.01)
*C12Q 1/6886*  (2018.01)
*G01N 33/574*  (2006.01)

(52) U.S. Cl.
CPC ..... *C12Q 1/6886* (2013.01); *G01N 33/57419* (2013.01); *C12Q 2600/118* (2013.01); *C12Q 2600/158* (2013.01); *G01N 2800/54* (2013.01)

(58) Field of Classification Search
None
See application file for complete search history.

(56) References Cited

PUBLICATIONS

Marisa (PLOS Medicine May 2013 vol. 10 Issue 5 e1001453 pp. 1-13).*
Orian-Rousseau (Int J Cancer 113 699-705 (2005)).*
Whitehead (Genome Biology 2005 vol. 6 Issue 2 Article R13).*
Hoshikawa et al (Physical Genomics 2003 vol. 12 pp. 209-219).*
Linn et al., "Differential Regulation of Androgen Receptor by PIM-1 Kinases via Phosphorylation-Dependent Recruitment of Distinct Ubiquitin E3 Ligases," *J. Biol. Chem.* 2012, 287; 22959-22968.
Lo et al., "Identification of Somatic Mutations of the RNF6 in Human Esophageal Squamous Cell Carcinoma," *Cancer Research* 62, 4191-4193, Aug. 1, 2022.
Lopez et al., "Gene Control in Germinal Differentiation: Rnf6, a Transcription Regulatory Protein in the Mouse Sertoli Cell," *Molecular and Cellular Biology*, May 2002, pp. 3488-3496.
MacDonald et al., "Cloning and Characterization of RNF6, a Novel RING Finger Gene Mapping to 13q12," *Genomics* 58, 94-97 (1999).
Tursun et al., "The Ubiquitin Ligase Rnf6 Regulates Local LIM Kinase 1 Levels in Axonal Growth Cones," *Genes Dev.*, 2005 19: 2307-2319.
Xu et al., "Regulation of Androgen Receptor Transcriptional Activity and Specificity by RNF6-Induced Ubiquitination," *Cancer Cell* 15, 270-282, Apr. 7, 2009.

* cited by examiner

*Primary Examiner* — James Martinell
(74) *Attorney, Agent, or Firm* — Kilpatrick Townsend & Stockton LLP

(57) ABSTRACT

The present invention provides a method for diagnosing of colorectal cancer in a subject and a method for determining risk of recurrence of colorectal cancer among colorectal cancer patients by detecting overexpression of the RNF6 gene, which in some cases is due to a higher than normal copy number of the genomic sequence of this gene. A kit and device useful for such methods are also provided. In addition, the present invention provides a method for treating colon cancer by suppressing RNF6 gene expression or activity.

13 Claims, 11 Drawing Sheets
Specification includes a Sequence Listing.

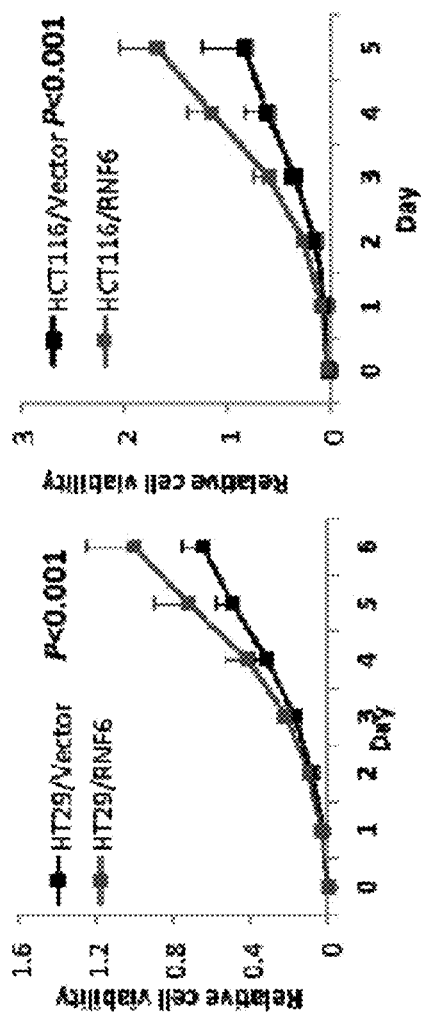
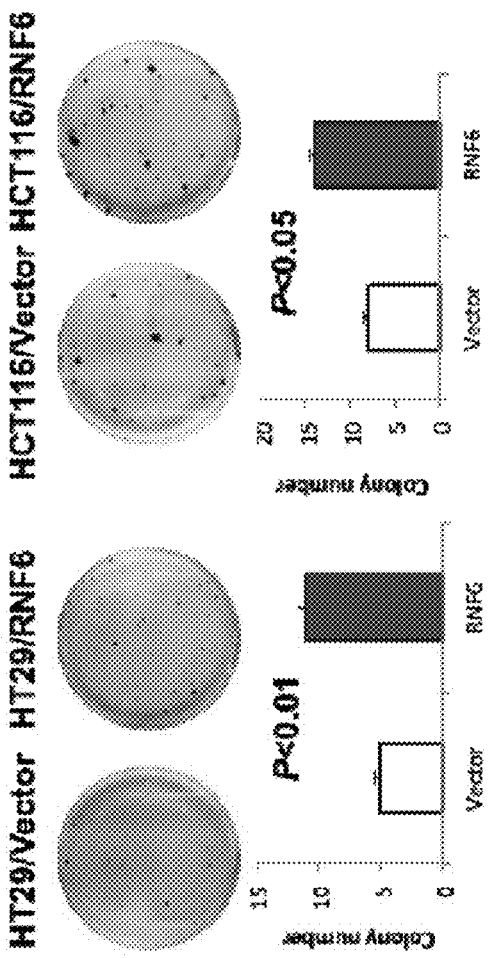
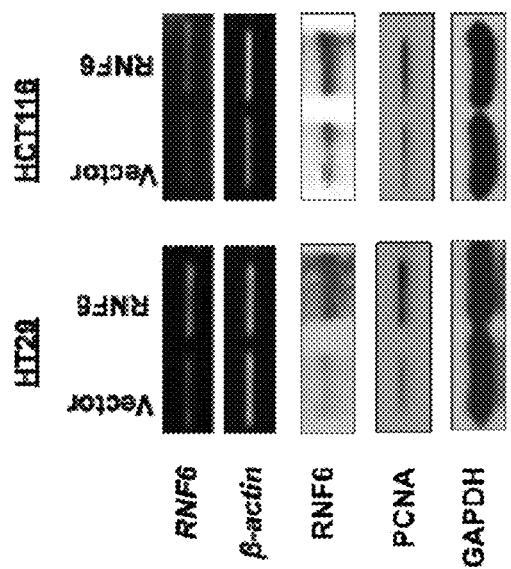
FIG. 4A

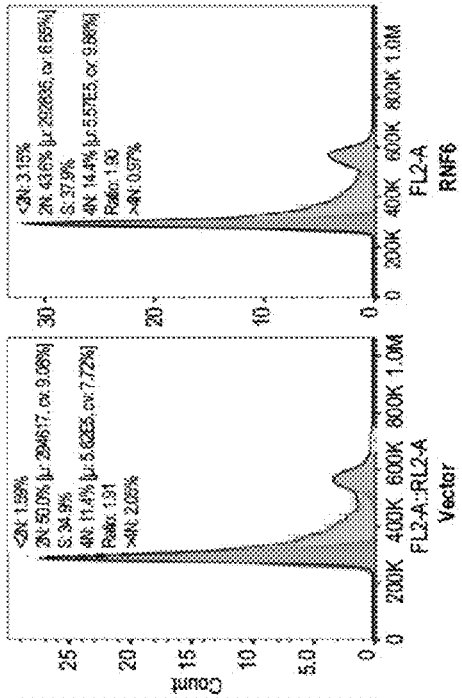
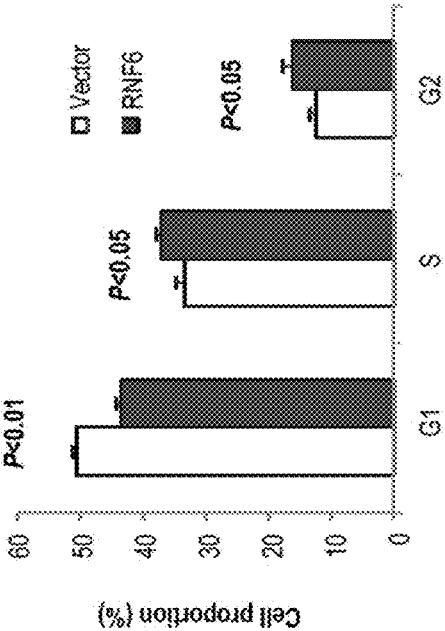
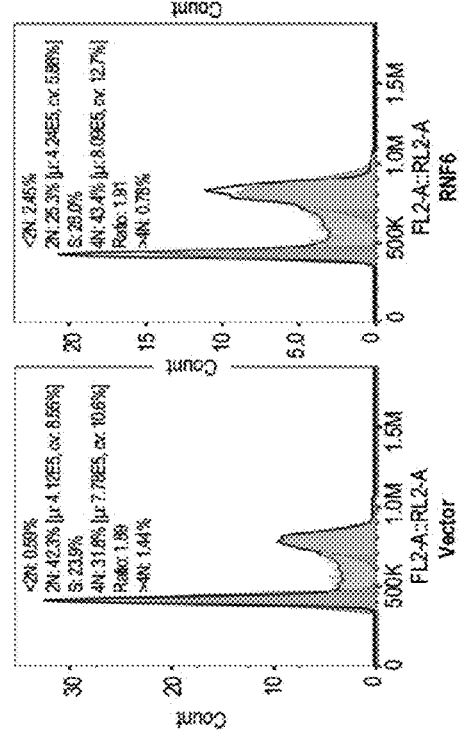
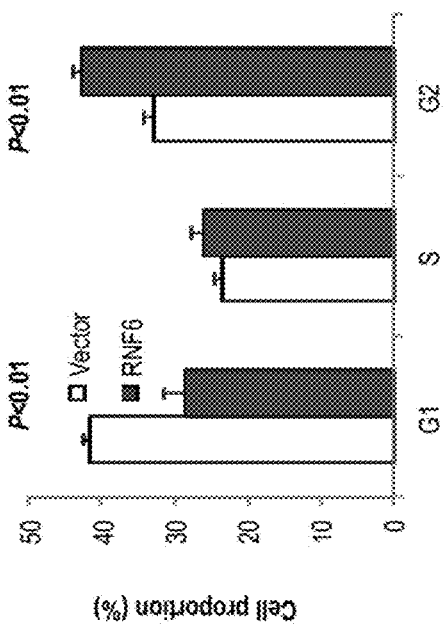
FIG. 5A1

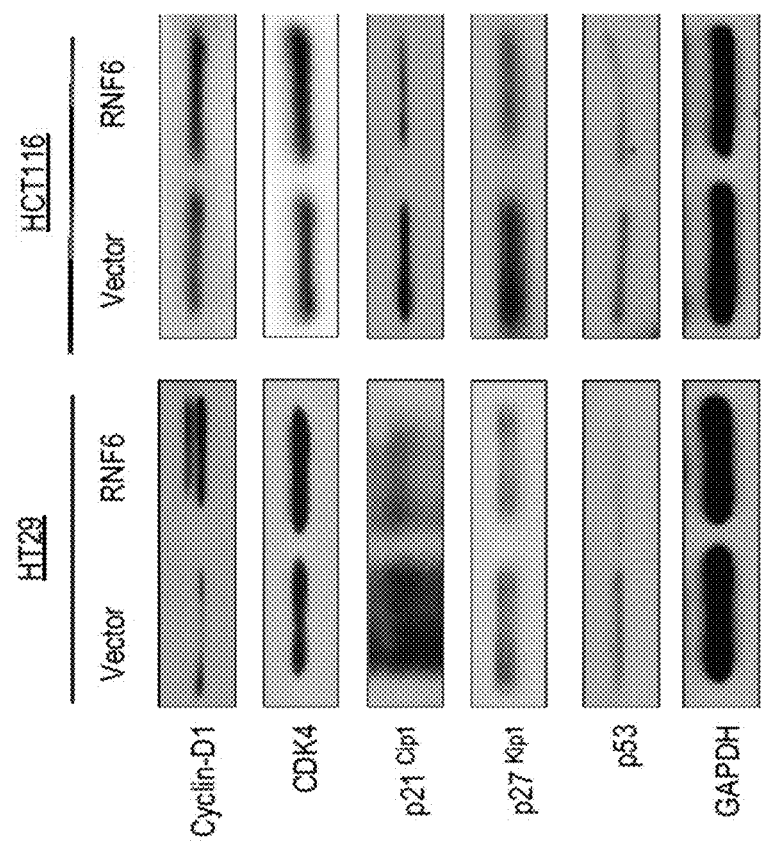
FIG. 5A2

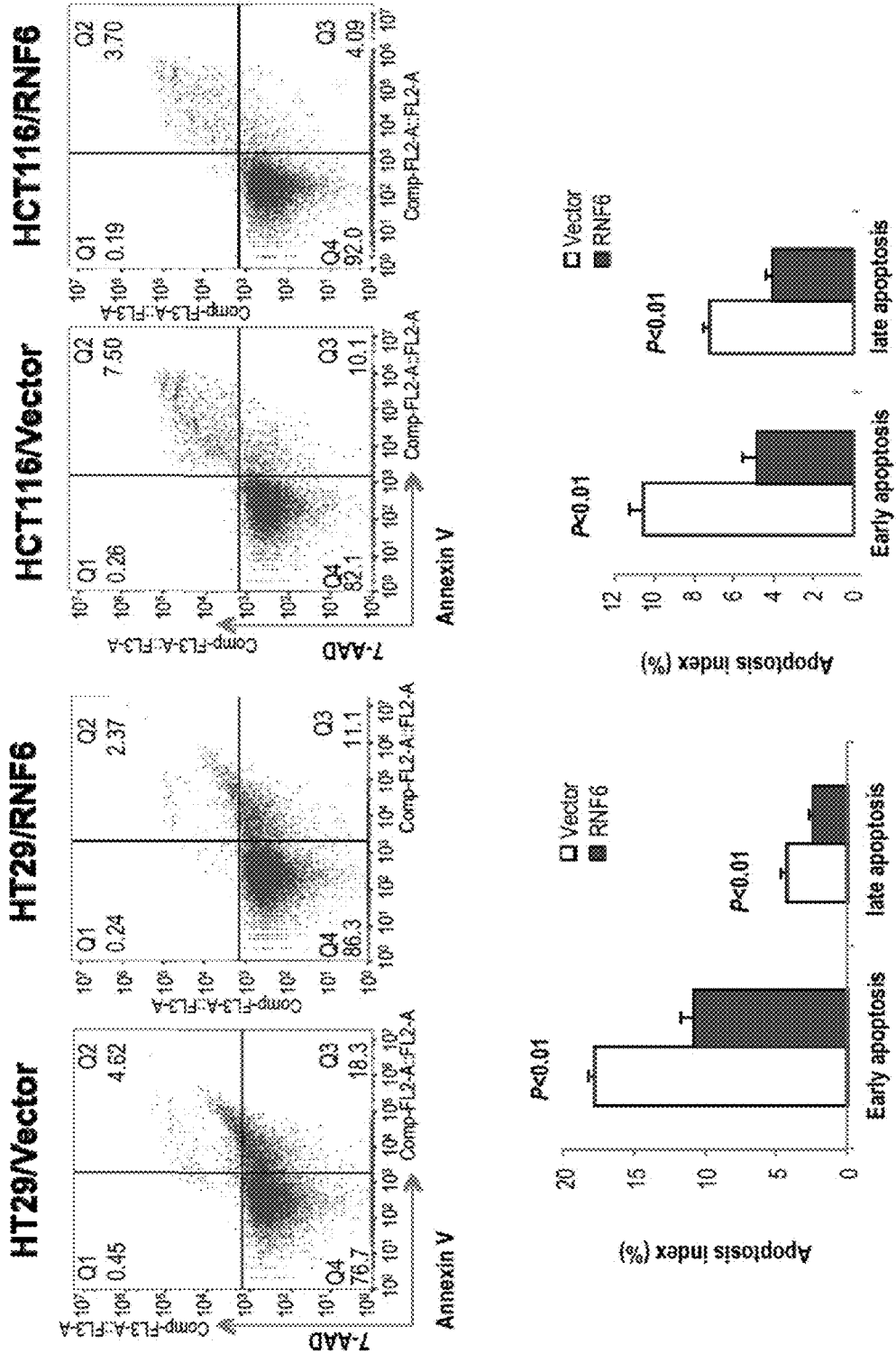
FIG. 5B1

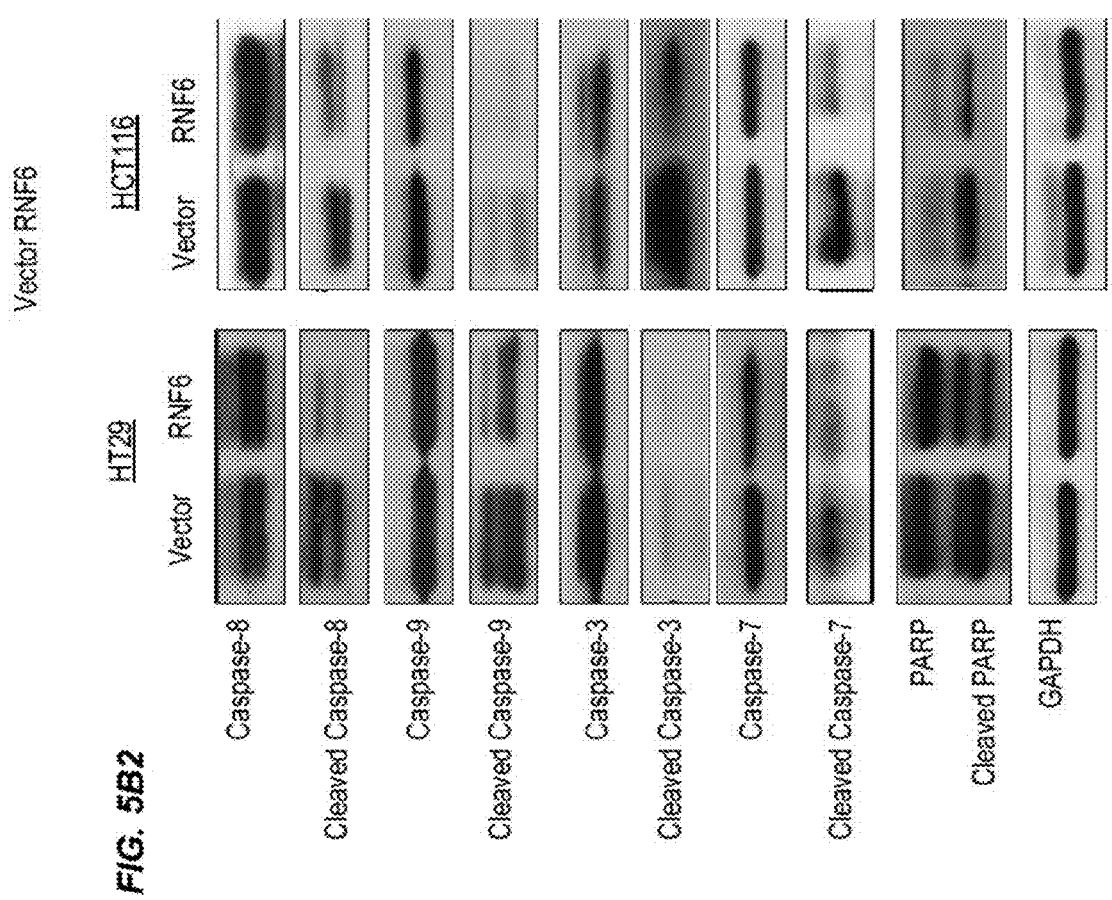
FIG. 5B2

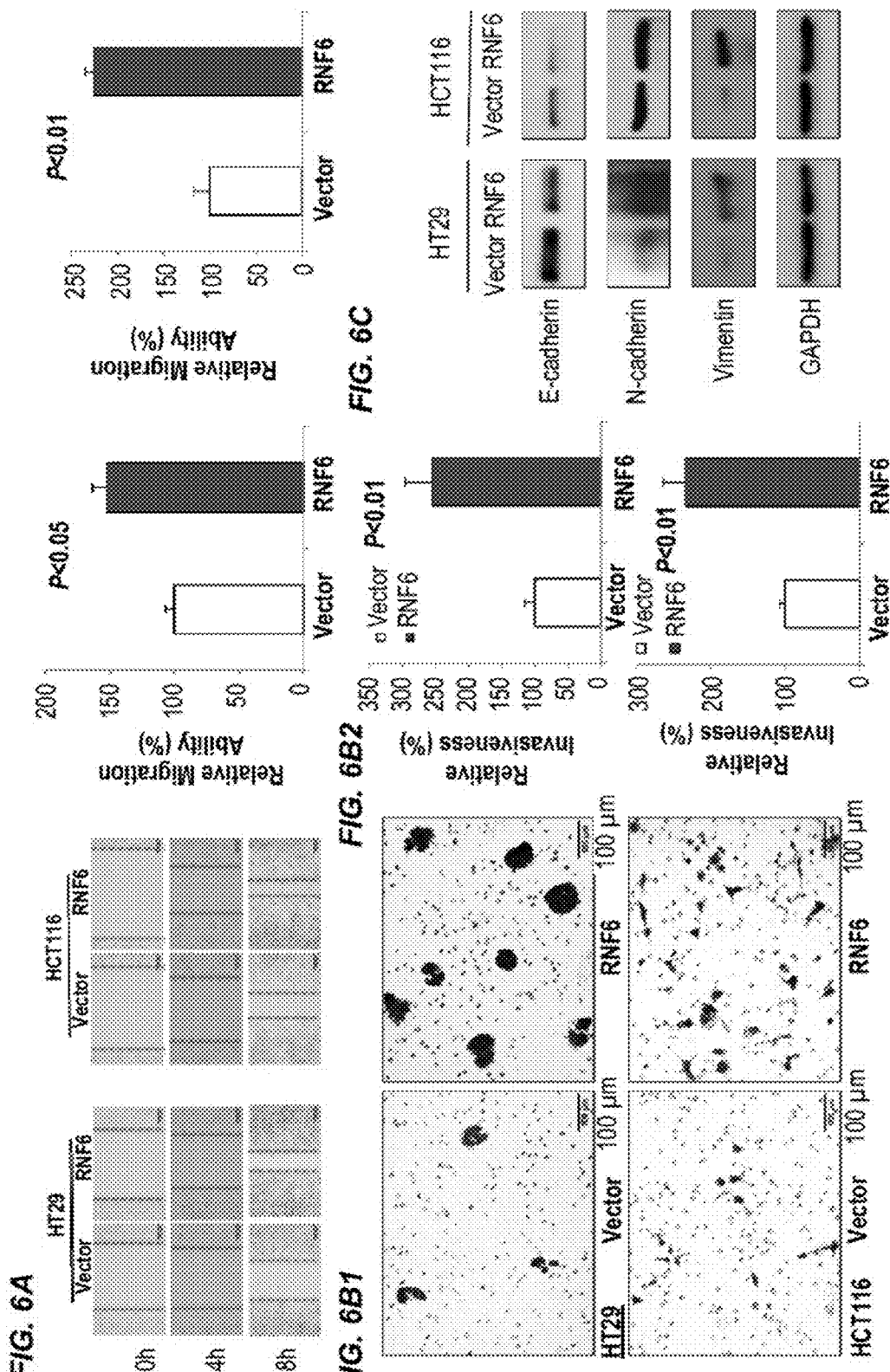

BIOMARKER RNF6 FOR COLORECTAL CANCER

BACKGROUND OF THE INVENTION

Colorectal cancer is the third most common cancer worldwide, accounting for about 10% of all cancer cases diagnosed annually. It is a deadly disease with serious impact on human health. During the year of 2012, for instance, 1.4 million new cases of colorectal cancers were diagnosed globally, and nearly 700,000 deaths from the disease were recorded. Incidence of colorectal cancers is substantially higher in developed countries, where more than 65% of cases are found. Men are more likely to suffer from this disease than women.

Diagnosis of colorectal cancer can be challenging. Although family history may provide useful implications for diagnosis, vast majority of the disease (greater than 75-95%) occurs in people with little or no genetic risk. Symptoms of colorectal cancer also can vary significantly, depending on the location of the cancer in the colon, and whether it has spread elsewhere in the body. Depending on how early colorectal cancer is diagnosed, its prognosis can vary from very good to very grim: it is highly curable with surgery when the cancer mass remains confined within the wall of the colon; on the other hand, once colorectal cancer has spread, it is usually not curable, with medical intervention focusing on improving quality of life and alleviating symptoms. On average, the 5-year survival rate in the United States is around 65%.

Because of the high prevalence of colorectal cancer and the vital importance of early diagnosis on patients' life expectancy, there exists an urgent need for new and more effective methods to diagnose, monitor, and treat colorectal cancer. This invention fulfills this and other related needs.

BRIEF SUMMARY OF THE INVENTION

The present inventors have identified human RNF6 as a novel oncogene and diagnostic/prognostic marker for human colorectal cancer (CRC). More specifically, the inventors show that, compared with normal individuals, a greater number of copies of RNF6 genomic sequence are found in biological samples of cancer tissues from CRC patients. Such increase in RNF6 gene copy number leads to overexpression of RNF6 at both mRNA and protein levels. Suppression of RNF6 expression inhibits cancer cell growth and induces programmed cell death. Higher protein/mRNA expression level of RNF6 and copy number of RNF6 genetic sequence closely correlate with the likelihood of colon cancer recurrence among CRC patients who have been diagnosed of the disease and received initial treatment and are therefore also useful as prognostic markers for colon cancer.

As such, in the first aspect, the present invention provides a method for assessing the risk for colon cancer in a subject, i.e., the likelihood of colon cancer being present in the subject and/or the likelihood of the subject developing the disease at a later time. The method includes the steps of: (a) measuring the level of RNF6 in a sample taken from the subject, and (b) comparing the level obtained in step (a) with a standard control. When an increase in the RNF6 level is detected as compared with the standard control, it indicates that the subject may have colon cancer or have an increased risk for colon cancer. Typically, the sample used in the method is a colon mucosa sample, e.g., one that includes colon epithelial cells. The subject being tested may be a human or a member of other mammals such as primates, who may or may not exhibit any signs indicative of any condition or abnormality relating to the colon.

In some embodiments, the level of RNF6 is the RNF6 protein level. In other embodiments, the level of RNF6 is RNF6 mRNA level. In yet other embodiments, the RNF6 level is the genomic DNA level of RNF6, or copy number of RNF6 gene or genomic sequence. When the RNF6 protein level is measured, step (a) may include an immunoassay using an antibody that specifically binds the RNF6 protein. For example, a Western Blot analysis may be used. In other cases, step (a) may involve mass spectrometry, or a hybridization-based assay such as hybridization to a microarray, fluorescence probe, or molecular beacon.

When RNF6 mRNA level or genomic sequence copy number is measured, step (a) in some cases may involve a polynucleotide amplification reaction, such as a polymerase chain reaction (PCR), especially a reverse transcriptase-PCR (RT-PCR) for mRNA detection or quantitative PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:3, 4, or 5 or a complement thereof. In some cases, the polynucleotide probe may include a detectable moiety.

In some embodiments, when the subject is indicated as having colon cancer or having an increased risk for developing colon cancer after the first round of method steps described above, the claimed method may further include repeating the same steps at a later time using the same type of sample from the subject. A decrease in RNF6 level, especially RNF6 expression level in mRNA or protein, at the later time as compared to the amount from the original step (a) indicates an improvement of colon cancer or a lessened risk for the disease, whereas an increase indicates a worsening of colon cancer or a heightened risk for the disease.

In a second aspect, the present invention provides a method for assessing likelihood of recurrence of colon cancer in a colon cancer patient, for example, after the patient has been diagnosed of the disease and already received treatment for the disease including surgery, radio- and/or chemotherapy. Likelihood of disease recurrence in a colon cancer patient can also be assessed by comparing RNF6 level, such as copy number of the RNF6 genomic sequence, the expression level of RNF6 mRNA or protein among patients who have been diagnosed with colon cancer. Briefly, the method for assessing likelihood of mortality includes the steps of: (a) measuring RNF6 level in a colon cancer sample taken from a first patient who has been diagnosed with colon cancer, and (b) comparing the RNF6 level obtained in step (a) with the RNF6 level determined in another sample of same type that was taken from a second colon cancer patient and measured in the same step (a). When the RNF6 level is higher in the first patient's sample than that found in the second patient's sample, the first patient is deemed as having a higher likelihood of recurrence from colon cancer than the second patient. Typically, the sample used in the method is a colon mucosa sample, e.g., one that includes colon epithelial cells. The subject being tested may be a human or a member of other mammals such as primates. In some cases, the second patient is one who has been diagnosed with colon cancer but has been previously determined as having a normal copy number for the RNF6 gene and/or a normal expression level of RNF6 mRNA and/or protein in the colon cancer tissue.

In some embodiments of this method, the RNF6 level is copy number of the RNF6 gene. In other embodiments, the RNF6 level is the RNF6 protein expression level. In other embodiments, the RNF6 level is RNF6 mRNA expression level. When the RNF6 protein level is measured, step (a) may include an immunoassay using an antibody that specifically binds the RNF6 protein. For example, a Western Blot analysis may be used. In other cases, step (a) may involve mass spectrometry, or a hybridization-based assay such as hybridization to a microarray, fluorescence probe, or molecular beacon.

When RNF6 genomic DNA or mRNA level is measured, step (a) in some cases may involve a polynucleotide amplification reaction, such as a PCR, especially an RT-PCR or quantitative PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:3, 4, or 5 or a complement thereof. In some cases, the polynucleotide probe may include a detectable moiety. The sample used in this method is a colon mucosa sample taken from confirmed cancerous tissues.

In a third aspect, the present invention provides a kit for detecting colon cancer or assessing risk of colon cancer or assessing risk of recurrence of colon cancer in a subject, comprising (1) a standard control that provides an average amount of RNF6 protein or RNF6 mRNA or an average copy number of RNF6 genomic sequence; and (2) an agent that specifically and quantitatively identifies RNF6 protein, RNF6 mRNA, or RNF6 genomic DNA. In some cases, the agent may be an antibody that specifically binds the RNF6 protein; or the agent may be a polynucleotide probe that specifically hybridizes with the RNF6 genomic DNA or RNF6 mRNA. For example, the polynucleotide probe hybridizes with at least a segment of SEQ ID NO:3, 4, or 5 or a complement thereof. The agent may include a detectable moiety. In other cases, the kit may further comprise two oligonucleotide primers for specifically amplifying at least a segment of SEQ ID NO:3, 4, or 5 or its complement in an amplification reaction. Typically, the kit will further include an instruction manual.

In a fourth aspect, the present invention provides a method for inhibiting growth of a colon cancer cell. The claimed method includes the step of contacting the colon cancer cell with an effective amount of an RNF6 inhibitor such that RNF6 gene copy number is reduced, RNF6 expression at mRNA and/or protein level is suppressed. In some embodiments, the RNF6 inhibitor comprises one or more gene-editing agents such those in a CRISPR system. In some embodiments, the RNF6 inhibitor is a neutralizing antibody of the RNF6 protein capable of reducing or blocking the RNF6 protein activity. In some embodiments, the inhibitor is a nucleic acid encoding a polynucleotide sequence at least partially complementary to RNF6 DNA or RNA sequence or a segment thereof and capable of suppressing RNF6 mRNA expression. For example, the nucleic acid may encode an antisense RNA, miRNA, or siRNA. In some embodiments, the nucleic acid is an expression cassette comprising a promoter operably linked to a nucleotide sequence complementary to a segment of SEQ ID NO:3, 4, or 5. Various promoters may be useful in this method, for example, the promoter may be an epithelium-specific promoter. In some embodiments, the colon cancer cell is within a patient's body.

In a related aspect, the present invention provides use of an RNF6 inhibitor for manufacturing a medicament for treating colon cancer. The RNF6 inhibitor, which may suppress RNF6 level by reducing RNF6 gene copy number, RNF6 mRNA expression level, RNF6 protein expression level, or RNF6 protein activity, can be formulated with one or more physiologically acceptable excipients for administration to a patient who has been diagnosed with colon cancer. The inhibitor may be a polynucleotide, such as an antisense RNA, miRNA, or siRNA targeting the RNF6 mRNA, or a polypeptide, such as a neutralizing antibody against the RNF6 protein.

BRIEF DESCRIPTION OF THE DRAWINGS

FIG. 4A through FIG. 4B show RNF6 promoted CRC cell growth in an embodiment.

FIG. 5A1 through FIG. 5B2 show shows ectopic expression of RNF6 decreased cell population at G1 phase and promoted cell cycle enter S phase and G2 phase and suppressed cell apoptosis in an embodiment.

FIG. 6A through FIG. 6C show overexpression of RNF6 enhanced cell migration and invasion in an embodiment.

DEFINITIONS

Figure 1A:
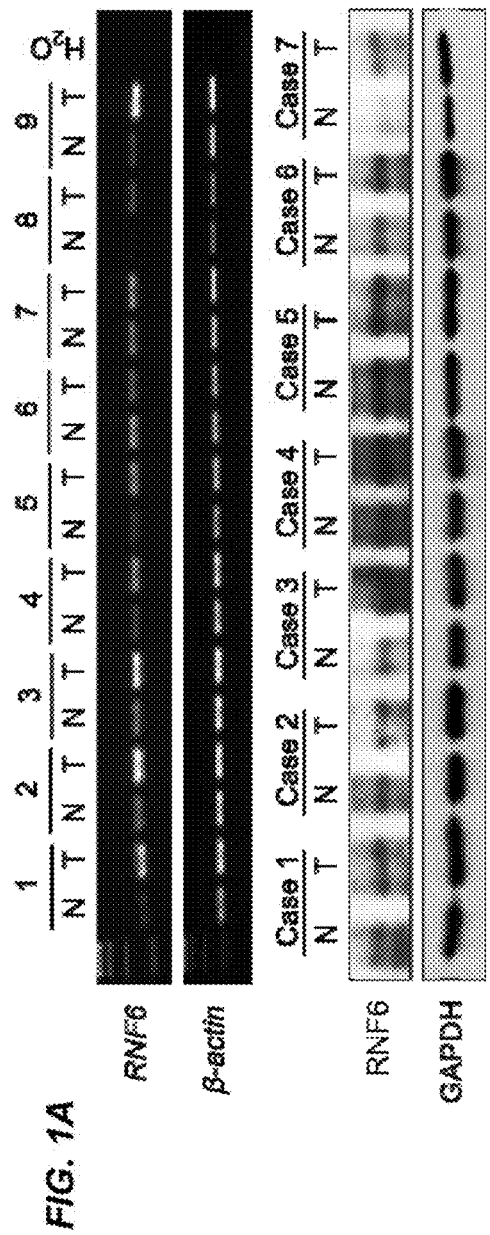
FIGS. 1A and 1B show the relative RNF6 expression level in paired samples of colorectal cancer tissues and adjacent normal tissues in an embodiment.

The term "RNF6 gene" or "RNF6 protein," as used herein, refers to any naturally occurring variants or mutants, interspecies homologs or orthologs, or man-made variants of human RNF6 gene or RNF6 protein. The DNA sequence for a human wild-type RNF6 mRNA is set forth in GenBank Accession No. NM_005977.3 (provided herein as SEQ ID NO:4), which translate to a coding sequence (provided herein as SEQ ID NO:3) for a 685-amino acid RNF6 protein (provided herein as SEQ ID NO:6). A RNF6 protein within the meaning of this application typically has at least 80%, or 90%, or 95% or higher sequence identity to the human wild-type RNF6 protein.

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human RNF6 protein) or the translation of a protein encoded by a polynucleotide sequence. In other words, both mRNA level and protein level encoded by a gene of interest (e.g., human RNF6 gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, colon biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, colon tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant RNF6 protein used in the method of this invention (e.g., for treating colon cancer) has at least 80% sequence identity, preferably 85%, 90%, 91%, 92%, 93, 94%, 95%, 96%, 97%, 98%, 99%, or 100% identity, to a reference sequence, e.g., a wild-type human RNF6 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)$'_2$, a dimer of Fab which itself is a light chain joined to $V_H$—$C_H1$ by a disulfide bond. The F(ab)$'_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of RNF6 mRNA or RNF6 protein found in non-cancerous colon tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within +10% of the standard control, or within ±5%, 2%, or even less variation from the standard control.

The term "inhibiting" or "inhibition," as used herein, refers to any detectable negative effect on a target biological process, such as cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., expression of RNF6 at either mRNA level or protein level) upon application of an inhibitor, when compared to a control where the inhibitor is not applied.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human RNF6 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., RNF6 genomic DNA, mRNA, or protein, that is present in an established normal disease-free tissue sample, e.g., a normal colon epithelial tissue sample. The standard control value is suitable for the use of a method of the present invention, to serve as a basis for comparing the amount of RNF6 genomic DNA, mRNA, or protein that is present in a test sample. An established sample serving as a standard control provides an average amount of RNF6 mRNA or RNF6 protein or an average copy number of RNF6 genomic sequence that is typical for a colon epithelial tissue sample (e.g., colon mucosa) of an average, healthy human without any colon disease especially colon cancer as conventionally defined, preferably without any increased risk of developing the disease. A standard control value may vary depending on the nature of the sample as well as other factors such as the gender, age, ethnicity of the subjects based on whom such a control value is established.

The term "average," as used in the context of describing a human who is healthy, free of any colon disease (especially colon cancer) as conventionally defined, refers to certain characteristics, especially the copies of RNF6 genomic sequence or amount of RNF6 mRNA or protein, found in the person's colon tissue, e.g., epithelial tissue or colon mucosa, that are representative of a randomly selected group of healthy humans who are free of any colon diseases (especially colon cancer) and free of known risk of developing the disease. This selected group should comprise a sufficient number of humans such that the average copy number and average amount of RNF6 mRNA or protein in the colon mucosa among these individuals reflects, with reasonable accuracy, the corresponding copy number of RNF6 gene and amount of RNF6 mRNA/protein in the general population of healthy humans. In addition, the selected group of humans generally have a similar age to that of a subject whose colon tissue sample is tested for indication of colon cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human RNF6 genomic DNA, RNF6 mRNA, or RNF6 protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding an RNF6 antisense RNA is the amount of said polynucleotide to achieve a decreased level of RNF6 mRNA or protein expression or biological activity, such that the symptoms, severity, and/or recurrence change of colon cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, colon cancer. Subjects also include individuals currently undergoing therapy that seek manipulation of the therapeutic regimen. Subjects or individuals in need of treatment include those that demonstrate symptoms of colon cancer or are at risk of suffering from colon cancer or its symptoms. For example, a subject in need of treatment includes individuals with a genetic predisposition or family history for colon cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of RNF6 protein are used to refer to inhibitory, activating, or modulating molecules, respectively, identified using in vitro and in vivo assays for RNF6 protein binding or signaling, e.g., ligands, agonists, antagonists, and their homologs and mimetics. The term "modulator" includes inhibitors and activators. Inhibitors are agents that, e.g., partially or totally block binding, decrease, prevent, delay activation, inactivate, desensitize, or down regulate the activity of RNF6 protein. In some cases, the inhibitor directly or indirectly binds to RNF6 protein, such as a neutralizing antibody. Inhibitors, as used herein, are synonymous with inactivators and antagonists. Activators are agents that, e.g., stimulate, increase, facilitate, enhance activation, sensitize or up regulate the activity of RNF6 protein. Modulators include RNF6 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Colorectal cancer patients often face a grim prognosis when the disease is detected in its later stages. Early detection of colorectal cancer is therefore critical for improving patient survival rate. Moreover, it is also of practical importance for patient survival to assess the likelihood of recurrence of colorectal cancer among patients who have already received a diagnosis of colorectal cancer and have received initial treatment such as surgical removal of the primary tumor mass, so that patients in need can be better monitored for potential recurrence of the disease and receive necessary additional treatment (e.g., additional surgical intervention, chemotherapy, and/or radiotherapy) as early as possible.

The present inventors discovered for the first time that increased copy number of genomic RNF6 sequence, and overexpression of RNF6, both at the mRNA and protein levels, are often observed in colorectal cancer cells. This overexpression of RNF6 protein is due to increased copy number in the RNF6 genomic sequence, which leads to increased transcription of RNF6 mRNA. This discovery provides important means for detecting, monitoring, and treating colorectal cancer. Generally, a higher than normal RNF6 gene copy number and mRNA/protein level seen in a test subject, who may or may not exhibit any signs of colon disorder or anomaly, indicates a high likelihood that the subject already has or will later develop colorectal cancer. Similarly, a higher RNF6 gene copy number or mRNA/protein level indicates a higher likelihood that a colorectal cancer patient who already has received treatment for colorectal cancer (such as surgical removal of the primary tumor mass, radiotherapy, and chemotherapy) will experience recurring colorectal cancer, in comparison to another colorectal cancer patient who has a lower RNF6 gene copy number and/or mRNA/protein level, for example, one who has a normal RNF6 gene copy number and/or normal mRNA/protein level compared healthy human subjects who do not have colorectal cancer and are not at any increased risk of developing the disease.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human RNF6 gene, and synthetic oligonucleotides (e.g., primers) can be verified using, e.g., the chain termination method for double-stranded templates of Wallace et al., *Gene* 16: 21-26 (1981).

III. Acquisition of Tissue Samples and Analysis of RNF6 mRNA or DNA

The present invention relates to measuring the amount of RNF6 mRNA or RNF6 genomic DNA found in a person's colon tissue, especially colon epithelial sample, as a means to detect the presence, to assess the risk of developing, and/or to monitor the progression or treatment efficacy of colon cancer, including assessing the likelihood of disease recurrence. Thus, the first steps of practicing this invention are to obtain a colon epithelial tissue sample from a test subject and extract mRNA or DNA from the sample.

A. Acquisition and Preparation of Colon Tissue Samples

A colon tissue sample is obtained from a person to be tested or monitored for colon cancer using a method of the present invention. Collection of colon epithelial tissue sample from an individual is performed in accordance with the standard protocol hospitals or clinics generally follow, such as during a colonoscopy. An appropriate amount of colon epithelium is collected and may be stored according to standard procedures prior to further preparation.

The analysis of RNF6 mRNA or DNA found in a patient's colon epithelial sample according to the present invention may be performed using, e.g., colon mucosa. The methods for preparing tissue samples for nucleic acid extraction are well known among those of skill in the art. For example, a subject's colon mucosa sample should be first treated to disrupt cellular membrane so as to release nucleic acids contained within the cells.

B. Extraction and Quantitation of DNA and RNA

Methods for extracting DNA from a biological sample are well known and routinely practiced in the art of molecular biology (e.g., described by Sambrook and Russell, *Molecular Cloning: A Laboratory Manual* 3d ed., 2001). RNA contamination should be eliminated to avoid interference with DNA analysis.

Likewise, there are numerous methods for extracting mRNA from a biological sample. The general methods of mRNA preparation can be followed, see, e.g., Sambrook and Russell, supra; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of DNA or mRNA Level

Once DNA or mRNA is extracted from a sample, the amount of human RNF6 genomic DNA or mRNA may be quantified. The preferred method for determining the DNA or mRNA level is an amplification-based method, e.g., by polymerase chain reaction (PCR), especially reverse transcription-polymerase chain reaction (RT-PCR) for mRNA quantitative analysis.

While RNF6 genomic DNA is directly subject to amplification, mRNA must be first reverse transcribed. Prior to the amplification step, a DNA copy (cDNA) of the human RNF6 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J Clin. Microbiol.* 33:1442-1447, 1995; and U.S. Pat. No. 5,075, 212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target genomic DNA or mRNA is typically used in practicing the present invention, one of skill in the art will recognize, however, that amplification of these DNA or mRNA species in a sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of DNA or mRNA in the sample. For a review of branched-DNA signal amplification for direct quantitation of nucleic acid sequences in clinical samples, see Nolte, *Adv. Clin. Chem.* 33:201-235, 1998.

2. Other Quantitative Methods

The RNF6 DNA or mRNA can also be detected using other standard techniques, well known to those of skill in the art. Although the detection step is typically preceded by an amplification step, amplification is not required in the methods of the invention. For instance, the DNA or mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target DNA or mRNA, the amount of which may then be compared to the control based on the intensity of the band. Alternatively, oligonucleotide probes specific to RNF6 DNA or mRNA can be used to detect the presence of such DNA or mRNA species and indicate the amount of DNA or mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Quantitation of Polypeptides

A. Obtaining Samples

The first step of practicing the present invention is to obtain a sample of colon epithelium from a subject being tested, assessed, or monitored for colon cancer, the risk of developing colon cancer, or the severity/progression/chances of recurrence of the condition. Samples of the same type should be taken from both a control group (normal individuals not suffering from any colorectal disorder especially neoplasia) and a test group (subjects being tested for possible colon cancer, for example). Standard procedures routinely employed in hospitals or clinics are typically followed for this purpose, as stated in the previous section.

For the purpose of detecting the presence of colon cancer or assessing the risk of developing colon cancer in test subjects, individual patients' colon mucosa samples may be taken and the level of human RNF6 protein may be measured and then compared to a standard control. If a decrease in the level of human RNF6 protein is observed when compared to the control level, the test subject is deemed to have colon cancer or have an elevated risk of developing the disease. For the purpose of monitoring disease progression or assessing therapeutic effectiveness in colon cancer patients, individual patient's colon epithelial samples may be taken at different time points, such that the level of human RNF6 protein can be measured to provide information indicating the state of disease. For instance, when a patient's RNF6 protein level shows a general trend of decrease over time, the patient is deemed to be improving in the severity of colon cancer or the therapy the patient has been receiving is deemed effective. A lack of change in a patient's RNF6 protein level or a continuing trend of increase on other hand would indicate a worsening of the condition and ineffectiveness of the therapy given to the patient. Generally, a higher RNF6 protein level seen in a patient indicates a more severe form of the colon cancer the patient is suffering from and a worse prognosis of the disease, as manifested in shorter life expectancy, higher rate of metastasis, resistance to therapy, higher chances of recurrence, etc. Among colon cancer patients, one who has a higher level of RNF6 protein expression in the colon cancer sample than that found in a second colon cancer patient has a higher likelihood of disease recurrence compared to the second patient for any defined time period, such as 1-5 years post-diagnosis.

B. Preparing Samples for RNF6 Protein Detection

The colon tissue sample from a subject is suitable for the present invention and can be obtained by well-known methods and as described in the previous section. In certain applications of this invention, colon mucosa may be the preferred sample type.

C. Determining the Level of Human RNF6 Protein

A protein of any particular identity, such as RNF6 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human RNF6 protein) can also be detected by gel electrophoresis (such as 2-dimensional gel electrophoresis) and western blot analysis using specific antibodies. Alternatively, standard immunohistochemical techniques can be used to detect a given protein (e.g., human RNF6 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human RNF6 protein) can be generated by known techniques.

Other methods may also be employed for measuring the level of RNF6 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any colon disease (especially any form of tumor such as colon cancer) as conventionally defined is first selected. These individuals are within the appropriate parameters, if applicable, for the purpose of screening for and/or monitoring colon cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/ concentration of human RNF6 genomic DNA, RNF6 mRNA, or RNF6 protein in the colon tissue sample obtained from the group can be reasonably regarded as representative of the normal or average level among the general population of healthy people. Preferably, the selected group comprises at least 10 human subjects.

Once an average value for the RNF6 genomic DNA, mRNA, or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Colon Cancer

By illustrating the correlation of over-expression of RNF6 mRNA/protein and colon cancer, the present invention further provides a means for treating patients suffering from colon cancer: by way of suppressing RNF6 mRNA or protein expression or inhibiting RNF6 protein's biological activity. As used herein, treatment of colon cancer encompasses reducing, reversing, lessening, or eliminating one or more of the symptoms of colon cancer, as well as preventing or delaying the onset of one or more of the relevant symptoms, including reducing mortality or likelihood of disease recurrence among patients who have already received initial treatment. Inhibitors of RNF6 can be of virtually any chemical and structural nature: they may be polypeptides (e.g., antibody, antibody fragment, aptamer), polynucleotides (e.g., antisense DNA/RNA, small inhibitory RNA, or micro RNA), and small molecules. As long as they possess confirmed inhibitory effect against RNF6 expression or activity, such inhibitors may be useful for inhibiting colon cancer cell proliferation and therefore useful for treating colon cancer.

A. Suppressing RNF6 Expression or Activity

1. Inhibitors of RNF6 mRNA

Suppression of RNF6 expression can be achieved through the use of nucleic acids siRNA, microRNA, miniRNa, lncRNA, antisense oligonucleotides, aptamer. Such nucleic acids can be single-stranded nucleic acids (such as mRNA) or double-stranded nucleic acids (such as DNA) that can translate into an active form of inhibitor of RNF6 mRNA under appropriate conditions.

In one embodiment, the RNF6 inhibitor-encoding nucleic acid is provided in the form of an expression cassette, typically recombinantly produced, having a promoter operably linked to the polynucleotide sequence encoding the inhibitor. In some cases, the promoter is a universal promoter that directs gene expression in all or most tissue types; in other cases, the promoter is one that directs gene expression specifically in epithelial cells, especially in colon epithelium. Administration of such nucleic acids can suppress RNF6 expression in the target tissue, e.g., colon epithelium. Since the human RNF6 gene sequence encoding its mRNA is known as GenBank Accession No. NM_005977.3 and provided herein as SEQ ID NO:4, and its cDNA sequence is provided herein as SEQ ID NO:3, one can devise a suitable RNF6-suppressing nucleic acid from the sequence, species homologs, and variants of these sequences.

2. Inhibitors of RNF6 Protein

Suppression of RNF6 protein activity can be achieved with an agent that is capable of inhibiting the activity of RNF6 protein. An in vitro assay can be used to screen for potential inhibitors of RNF6 protein activity based in the binding between RNF6 protein and a candidate compound. Once a compound is identified in the binding assay, further testing may be conducted to confirm and verify the compounds capability to inhibiting RNF6 protein activity. In general, such an assay can be performed in the presence of RNF6 protein or a fragment thereof, for example, a recombinantly produced RNF6 protein or fragment, under conditions permitting its binding to a potential binding partner. For convenience, the RNF6 protein or the candidate compound may be immobilized onto a solid support and/or labeled with a detectable moiety. A third molecule, such as an antibody (which may include a detectable label) to RNF6 protein, can also be used to facilitate detection.

In some cases, the binding assays can be performed in a cell-free environment; whereas in other cases, the binding assays can be performed within a cell or on the cell surface, for example, using cells recombinantly or endogenously expressing an appropriate RNF6 polypeptide.

The anti-cancer effects of an RNF6 protein inhibitor of the present invention can also be demonstrated in in vivo assays. For example, an RNF6 protein inhibitor can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. Tumors development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

As stated above, RNF6 protein inhibitors can have diverse chemical and structural features. For instance, an inhibitor can be a non-functional RNF6 protein mutant that retaining the binding ability of RNF6 protein to its cofactors or other binding partners, an antibody to the RNF6 protein that interferes with RNF6 protein activity (e.g., a neutralizing antibody), or any small molecule or macromolecule that simply hinders the interaction between RNF6 protein and its cofactors or other binding partners. Essentially any chemical compound can be tested as a potential inhibitor of RNF6 protein activity. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. Pharmaceutical Compositions

1. Formulations

Compounds of the present invention are useful in the manufacture of a pharmaceutical composition or a medicament. A pharmaceutical composition or medicament can be administered to a subject for the treatment of colon cancer.

Compounds used in the present invention, e.g., an inhibitor of RNF6 mRNA or protein (e.g., a neutralizing antibody against RNF6 protein), a nucleic acid encoding a polynucleotide or polypeptide inhibitor for RNF6 gene expression or RNF6 protein activity (e.g., an expression vector encoding a neutralizing antibody against RNF6 protein), are useful in the manufacture of a pharmaceutical composition or a medicament comprising an effective amount thereof in conjunction or mixture with excipients or carriers suitable for application.

An exemplary pharmaceutical composition for suppressing RNF6 expression comprises (i) an express cassette comprising a polynucleotide sequence encoding an inhibitor of RNF6 protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

An RNF6 inhibitor or a nucleic acid encoding an RNF6 inhibitor can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng. 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., an RNF6 inhibitor or a nucleic acid encoding an RNF6 inhibitor, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., an RNF6 inhibitor or a nucleic acid encoding an RNF6 inhibitor, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that decreases the level or activity of RNF6 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control colon cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of RNF6 inhibitor or nucleic acid encoding an RNF6 inhibitor will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for an RNF6 inhibitor or a nucleic acid encoding an RNF6 inhibitor described herein are provided. Dosage for a RNF6 inhibitor-encoding nucleic acid, such as an expression cassette, can be between 0.1-0.5 mg/eye, with intravitreous administration (e.g., 5-30 mg/kg). Small organic compounds inhibitors can be administered orally at between 5-1000 mg, or by intravenous infusion at between 10-500 mg/ml. Monoclonal antibody inhibitors can be administered by intravenous injection or infusion at 50-500 mg/ml (over 120 minutes); 1-500 mg/kg (over 60 minutes); or 1-100 mg/kg (bolus) five times weekly. RNF6 protein or mRNA inhibitors can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical antiinflammatories, pain relievers, anti-histamines, anesthetic compounds, and the like. The additional therapeutic compound can be administered at the same time as, or even in the same composition with, main active ingredient (e.g., an RNF6 inhibitor or a nucleic acid encoding an RNF6 inhibitor). The additional therapeutic compound can also be administered separately, in a separate composition, or a different dosage form from the main active ingredient. Some doses of the main ingredient, such as an RNF6 inhibitor or a nucleic acid encoding an RNF6 inhibitor, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess RNF6 level, both at the levels of RNF6 mRNA and protein, as well as in the number of copies of RNF6 genomic sequence, in a subject, which can be used for various purposes such as detecting or diagnosing the presence of colon cancer, determining the risk of developing colon cancer, and monitoring the progression of colon cancer in a patient, including assessing the likelihood of recurrence of colon cancer among patients who have received a diagnosis of the disease and may have been treated, e.g., by surgery, chemotherapy, and/or radiotherapy.

Kits for carrying out assays for determining RNF6 mRNA level or RNF6 gene copy number typically include at least one oligonucleotide useful for specific hybridization with at least one segment of the RNF6 coding sequence or its complementary sequence. Optionally, this oligonucleotide is labeled with a detectable moiety. In some cases, the kits may include at least two oligonucleotide primers that can be used in the amplification of at least one segment of RNF6 DNA or mRNA by PCR, particularly by RT-PCR. Table 1 provides some examples of such primers.

Kits for carrying out assays for determining RNF6 protein level typically include at least one antibody useful for specific binding to the RNF6 protein amino acid sequence. Optionally, this antibody is labeled with a detectable moiety. The antibody can be either a monoclonal antibody or a polyclonal antibody. In some cases, the kits may include at least two different antibodies, one for specific binding to the RNF6 protein (i.e., the primary antibody) and the other for detection of the primary antibody (i.e., the secondary antibody), which is often attached to a detectable moiety.

Typically, the kits also include an appropriate standard control. The standard controls indicate the average value of RNF6 protein or mRNA or an average copy number of the RNF6 genomic sequence in the colon tissue (e.g., epithelium) of healthy subjects not suffering from colon cancer or any increased risk of developing colon cancer. In some cases such standard control may be provided in the form of a set value. In addition, the kits of this invention may provide instruction manuals to guide users in analyzing test samples and assessing the presence, risk, or likelihood of recurrence of colon cancer in a test subject.

In a further aspect, the present invention can also be embodied in a device or a system comprising one or more such devices, which is capable of carrying out all or some of the method steps described herein. For instance, in some cases, the device or system performs the following steps upon receiving a colon tissue sample, e.g., a colon mucosa sample taken from a subject being tested for detecting colon cancer, assessing the risk of developing colon cancer, or monitored for progression of the condition: (a) determining in sample the amount or concentration of RNF6 mRNA or protein, or the number of copies of RNF6 genomic sequence; (b) comparing the amount/concentration or copy number with a standard control value; and (c) providing an output indicating whether colon cancer is present in the subject or whether the subject is at risk of developing colon cancer, or whether there is a change, i.e., worsening or improvement, in the subject's colon cancer condition, or whether the patient has an increased likelihood of recurrence colon cancer, e.g., after the initial diagnosis and/or treatment. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Introduction

The current invention is based on the identification of the oncogene RNF6 and its role in colon cancer. Genomic DNA amplification and overexpression of RNF6 at the mRNA and/or protein level can serve as new diagnostic markers as well as to provide prognostic information relating to the likelihood of colon cancer recurrence in patients who have been diagnosed with the disease and received treatment such as surgical intervention for the disease. Emerging evidence indicates that CRC development is a multistep process with the accumulation of genetic and epigenetic alterations. Copy number aberrations (CNAs), including chromosome gains and losses, or localized amplifications and deletions, are frequently found in human CRC and are major causes of aberrant activation of oncogenes and inactivation of tumor suppressor genes. Some CNAs are closely related to clinical outcome or metastatic progression. It is of great importance to identify and functionally characterize novel genes with CNAs that are associated with CRC. In addition, identification of novel oncogene may identify potential biomarkers for tumor diagnosis and predictors of postoperative recurrence or treatment of CRC patients. By the TCGA somatic DNA copy number variation analysis in primary colon cancer tissues, the gene Ring Finger Protein 6 (RNF6) was identified to be preferentially amplified in colon cancer, which function remains largely uncharacterized. Overexpression of RNF6 appears to play a pivotal oncogenic role in colorectal carcinogenesis.

Figure 1B:
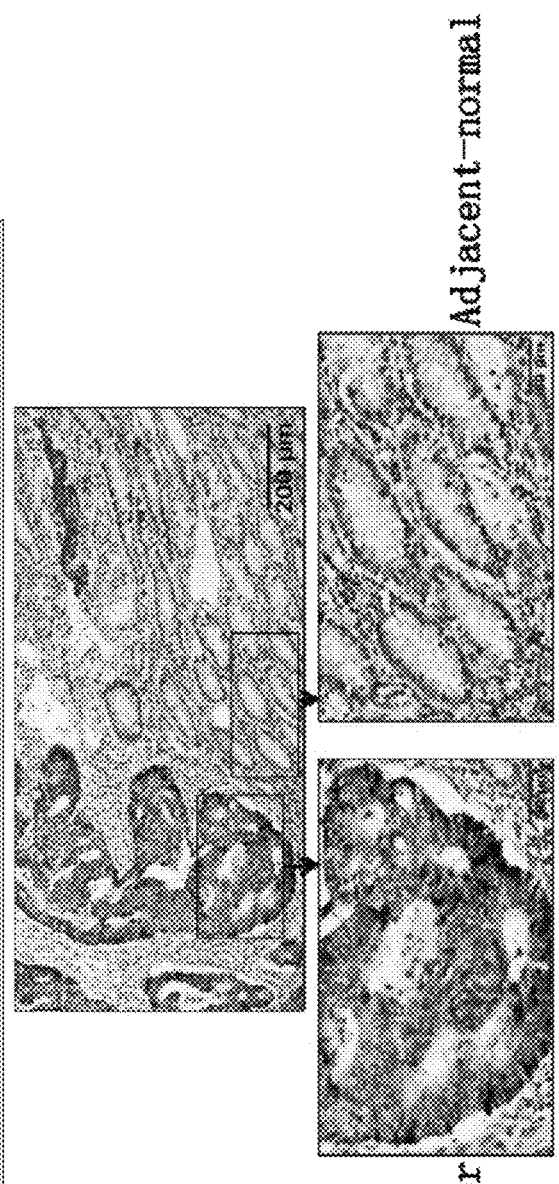
Figure 2:
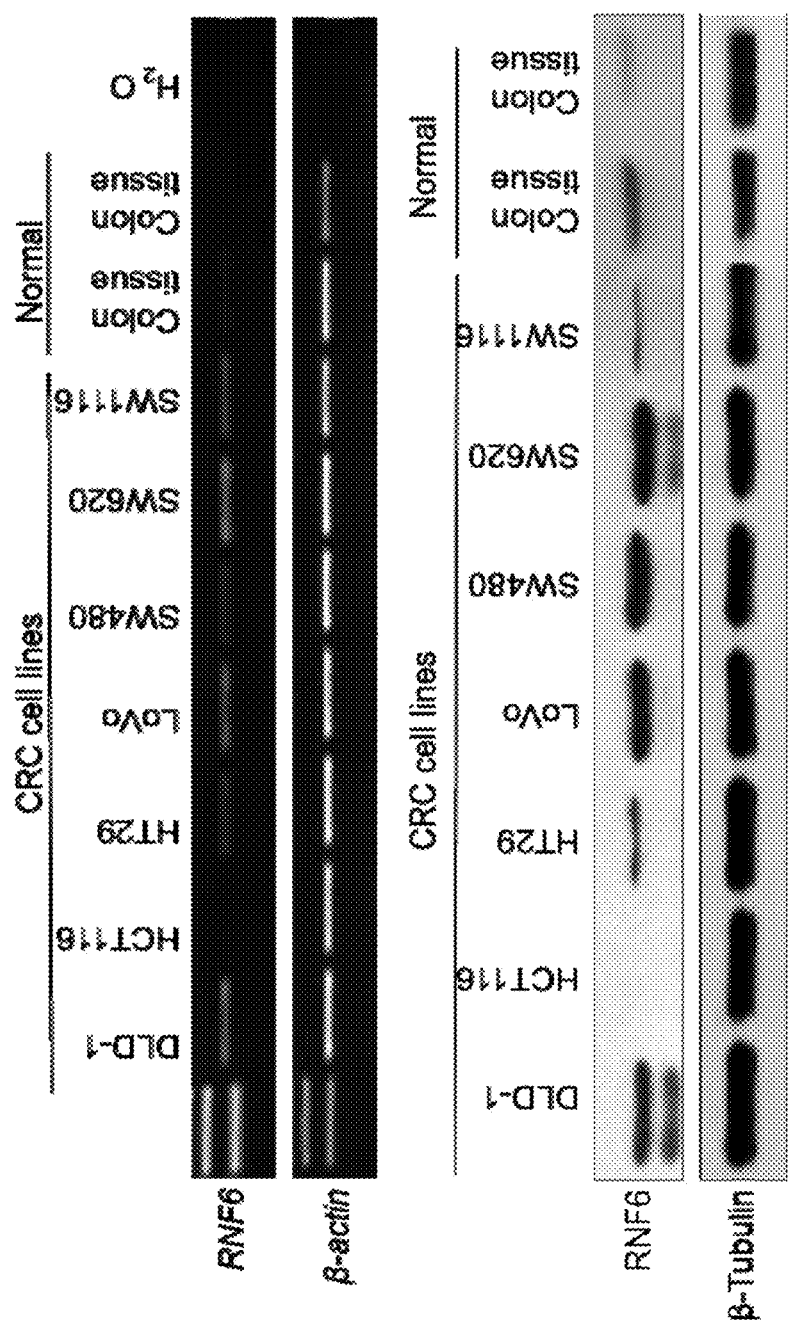
FIG. 2 shows RNF6 mRNA expression in colorectal cell lines and normal tissues in an embodiment.

The present inventors discovered that RNF6 was upregulated in CRC cell lines and CRC human tissues compared to normal control (FIGS. 1 and 2). Ectopic expression of RNF6 could promote CRC cell growth and inhibit cell apoptosis and cell death in vitro (FIGS. 4A-4B and FIGS.

5A1-5B2). Besides, RNF6 promoted the tumor migration and invasion in vitro as well (FIGS. 6A-6C).

Clinical application of RNF6 copy number status was evaluated in 118 primary CRCs. Amplification of RNF6 was detected in 33% (39/118) of primary CRCs. Moreover, the amplification of RNF6 was positively associated with its mRNA overexpression in the 118 CRC tissues (R sq=0.4857; P<0.0001; FIG. 3B).

Figure 7:
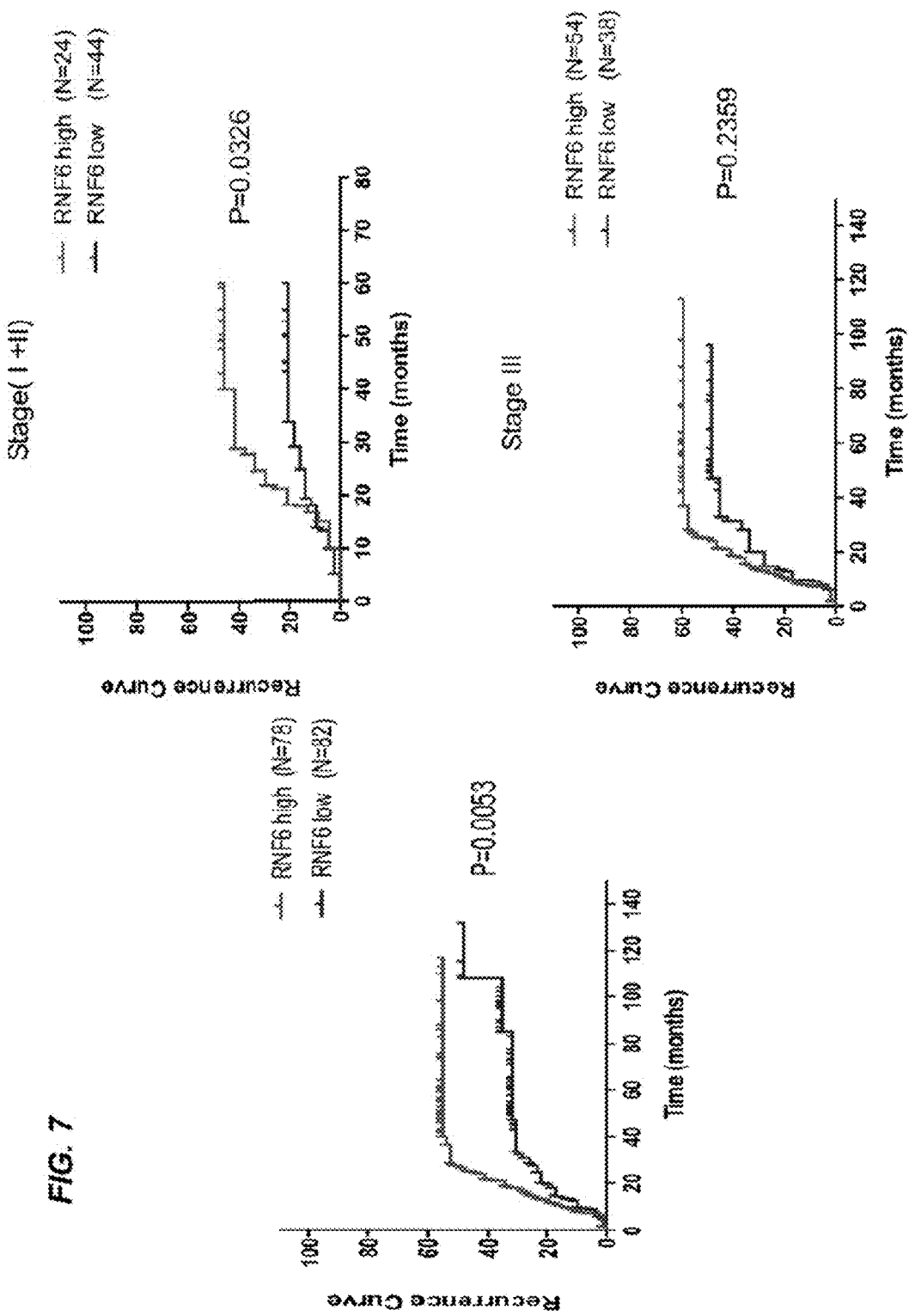
FIG. 7 shows upregulated expression of RNF6 served as an independent predictor of CRC recurrence in an embodiment.

The association of RNF6 mRNA and clinicopathological features including clinical outcome was analysed in 160 patients with colorectal cancer. There was no correlation between RNF6 high expression and clinicopathological features such as age, gender, tumor localization, differentiation of CRC patients (Table 3). After adjustment for potential confounding factors including age, gender and TNM stage, high expression of RNF6 was found to predict high recurrence risk of patients with colorectal cancer independently by multivariate Cox regression analysis (RR 1.653, 95% CI 1.016 to 2.690; P=0.043, Tables 4-5). As shown in the Kaplan-Meier survival curves, colorectal cancer patients with high expression of RNF6 had significantly higher recurrence risk than RNF6 low expression group (P=0.0053, log-rank test; FIG. 7). Therefore, the results of this study indicated that overexpression of RNF6 was an independent predictor of CRC recurrence.

In brief, the oncogenic function of RNF6 could potentially be applied to therapeutic intervention. Overexpression of RNF6 is associated with a great risk of colon cancer recurrence and it could be regarded as a prediction marker for the prognosis of postoperative patients. Utilizing this information, individual who are deemed to have an increased likelihood of developing recurring colon cancer after receiving initial therapy (such as surgical intervention to remove the tumor mass) could be screened regularly for early detection of the disease should it recur. Early detection of recurring colon cancer allows for patients a broader ranges of choices in terms of effective and appropriate therapeutic methods including but not limited to further surgery, chemotherapy, and radiotherapy, so as to improve patients' chances of long term survival from this deadly disease.

Materials and Methods

Human Colon Specimens

Tissue Samples

Surgically excised CRC tissues were obtained from 118 CRC patients from Peking University Cancer Hospital, Beijing, China. In addition, 49 paired CRC tissues and adjacent non-tumor colon tissues were obtained from Prince of Wales Hospital, Hong Kong, China. Tumor was staged according to the TNM staging system. Patients were being regularly followed up and the median follow-up duration since the time of diagnosis was 49.3 months (range 12.4 to 85.3 months). Written consent forms were obtained prior to tissue collection. The study was approved by the Human Ethics Committee of Peking University Cancer Hospital and the Ethics Committee of the Chinese University of Hong Kong.

Tumor Cell Line

Ten colon cell lines (DLD-1, HCT116, HT-29, LOVO, SW480, SW620 and SW1116) were obtained from the American Type Culture Collection (ATCC, Manassas, Va.). RPMI 1640 medium (Gibco BRL, Rockville, Md.) was used except HCT116 in McCoy's 5A medium supplemented with 10-20% fetal bovine serum (Gibco BRL). All cells were incubated with 5% of CO2 at 37° C.

Gene Expression Analysis

RNA Isolation

Total RNA was isolated using Qiazol reagent (Qiagen, Valencia, Calif., USA). First, about $5$-$10 \times 10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until using.

cDNA Synthesis

MultiScribe Reverse Transcriptase Kit (Applied Biosystems, Foster City, Calif., USA) was used to synthesize cDNA. The reaction mixture contained 1×Reverse Transcriptase buffer, 1×dNTP, 1×random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until further application.

Real-Time PCR

Real-time PCR was performed using SYBR Green master mixture (Roche, Indianapolis, Ind.) on Light Cycler 480 Instrument. Each sample was tested in triplicate. ΔΔCT method was employed to determine the fold change in gene expression level. ΔCT method was employed to determine the relative expression levels of corresponding genes. RNF6 specific primers were designed to test RNF6 mRNA expression in the CRC tissues. The mixture for PCR contained 2×SYBR Green PCR Master Mix 25 ul, Forward Primer 1 ul, Reverse Primer 1 ul, Nuclease-free water 21 ul and 20 ng qualified cDNA. The total volume is 15 ul for 96-well plate per well. The PCR program was 95° C. for 10 min, followed by 50 cycles (95° C. for 15 sec, 60° C. for 60 sec) of amplification, with a final extension at 4° C. for 10 min. All primers used to amplify the transcripts are listed in Table 1.

Immunohistochemistry

Paired primary tumor and adjacent non-tumor samples were obtained from CRC patients after surgical resection. Tissue types (tumor or normal) were assessed by histological staining. The remaining tissue specimens were fixed in 10% of formalin and embedded in paraffin. Immunohistochemistry was performed on five-micrometer paraffin sections using anti-RNF6 antibodies (Sigma-Aldrich, SAINT LOUIS, Colo.) with dilution of 1:100. The percentages of cells with positive labeling were used as immunohistochemical scores. The ethics committee of the Chinese University of Hong Kong approved of this study, and written consents were obtained from all patients involved.

DNA Copy Number Variation Analysis

Genomic DNA Extraction

Genomic DNA from CRC cell lines and tissue samples were isolated by using DNA mini kit (Qiagen) according to the kit protocol. Briefly, about 25 mg samples were lysed in 180 μl of QIAamp ATL buffer and 20 μl of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μl of AL buffer was added to the lysate and samples were incubated for 10 min at 70° C. After adding 200 μl of absolute ethanol, the solution was mixed by pulse-vortexing for 15 s. Then lysates were purified over a QIAamp column as specified by the manufacturer. The genomic DNA was diluted in 200 μl DNase-free $H_2O$. The quality and quantity of DNA were determined by measuring absorbance at 260 nm/280 nm using NanoDrop ND-1000 (NanoDrop).

DNA Copy Number Real-Time PCR

Real-time PCR was performed using TaqMan Copy Number master mixture (Roche, Indianapolis, Ind.) on ViiA™ 7 Real-Time PCR instrument. Each sample was tested in triplicate. RNF6 specific probe was used to assess DNA copy number status in the CRC tissues. The mixture for PCR contained 2×TaqMan Genotyping Master Mix 5 ul, 20×TaqMan Copy Number Assay 0.5 ul, 20×TaqMan Copy Number Reference Assay 0.5 ul, Nuclease-free water 4 ul and 10 ng purified genomic DNA. The total volume is 10 ul for 384-well plate per well. The PCR program was 95° C. for 10 min, followed by 40 cycles (95° C. for 15 sec, 60° C. for 60 sec) of amplification, with a final extension at 4° C. for 10 min.

Biological Function Analysis

Cloning of RNF6 and Construction of Expression Vector

The full-length cDNA of RNF6 gene expression vector was generated by PCR-cloning. Total RNA from normal human colon (Ambion, Austin, Tex., USA) was reverse transcribed into cDNA. Sequence corresponding to the open reading frame (ORF) of RNF6 was amplified by PCR. PCR product was cloned into the pCDNA3.1 expression vector.

RNF62 Gene Transfection and RNA Interference

Cells were seeded at ~6×10$^5$ cells on a 6-well plate without antibiotics for about 24 hr till the cell density reached about 90% confluence. Cells were then transfected with 2 μg RNF6 or control vector (pCDNA3.1) using Lipofectamine 2000 (Invitrogen). Lipofectamine 2000 (6.0 μL) diluted in 125 μL Opti-MEM (Invitrogen) was incubate at room temperature for 5 min. Then, plasmid DNA diluted in 125 μL Opti-MEM was combined with the Lipofectamine mixture. After 24-48 hr incubation at 37° C. in a 5% $CO_2$ incubator, cells were harvested for testing of transgenic expression. For stable cell lines, cells were passaged at a 1:10 ratio into fresh growth medium with proper concentration of neomycin (G418) (Invitrogen). Stable transfection cells were harvested after 14-21 days of selection for functional assays.

Knockdown RNF6 in SW480 and DLD-1 cell lines was performed by a shRNA targeting RNF6. Both SW480-RNF6 shRNA and DLD-1-RNF6 shRNA and shRNA control cells were selected for 2 weeks with neomycin after transfection 48 h. The cells were ready for further experiments.

Cell Viability Assay

Cell viability of stably transfected cells was examined using the Vybrant MTT Cell viability Assay Kit (Invitrogen, Carlsbad, Calif.) according to the manufacturer's instructions. All experiments were conducted three times in triplicates. Results were shown as the means±SD.

Colony Formation Assay

Two days after transfection, cells were subsequently split at 1:20 ratio on six-well plates with RPMI1640 in 10% FBS containing 500 μg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

Annexin Vapoptosis Assay

Annexin V is a protein that could bind the cell membrane after apoptosis have occurred and before membrane integrity has been lost. The proportion of apoptotic cells was evaluated using Annexin V and 7-amino-actinomycin (7-AAD) double staining. Briefly, the cells were washed with 1×PBS was resuspended in 100 μL ice-cold annexin-binding buffer (10 mM HEPES, 140 mM NaCl and 2.5 mM $CaCl_2$, pH 7.4) containing 5 μL Annexin V conjugated with Alexa Fluor 488 (Invitrogen) and 2 μL 7-AAD staining. After incubation for 15 min at room temperature, cells were mixed with additional 400 μL of ice-cold annexin-binding buffer and analyzed using flow cytometry.

Cell Cycle Analysis

The transient transfected CRC cells (HCT116 and HT29) were fixed in 70% ethanol-PBS for 24 hours. The cells were then labeled with 50 μg/ml of propidium iodide (BD Pharmingen, Franklin Lakes, N.J.). The cells were sorted by FACSCalibur (BD Biosciences, San Diego, Calif.). Cell-cycle profiles were analyzed by ModFit 3.0 software (BD Biosciences). All experiments were conducted three times in triplicates.

Wound-Healing Assay

Cell migration was assessed using the wound-healing assay. HCT116 and HT29 cells stably transfected with pcDNA3.1 or pcDNA3.1-RNF6 were cultured in six-well plates. When the cells reached 80% confluence, three scratch wounds in each well were made using a P-200 pipette tip. Fresh medium supplemented with reduced (5%) fetal bovine serum was then added, and the wound-closure was observed for 48 hours. Photographs were taken at 0, 24 and 48 hours, respectively.

Matrigel Invasion Assays

The stable transfected CRC cells (HCT116 and HT29) were seeded in a Matrigel-coated chamber (Becton Dickinson, Waltham, Mass., USA). After 48 h, cells that transferred into the lower surface of the insert were stained with crystal violet. Experiments were conducted in triplicate.

Western Blot Analysis

Total protein or nuclear protein was extracted and protein concentration was measured by the DC protein assay method of Bradford (Bio-Rad, Hercules, Calif.). Thirty micrograms of protein from each sample were separated on 12% SDS-PAGE and transferred onto nitrocellulose membranes (GE Healthcare, Piscataway, N.J.). Blots were immunostained with primary antibody and secondary antibody, respectively.

Statistical Analysis

The results were expressed as mean±SD. The Manne-Whitney U test was performed to compare the difference of RNF6 protein expression between tumor and adjacent non-tumor tissues. Patient age (at entry to follow-up) by vital status was compared using the t test. The Chi-Squared test was used for comparison of patient characteristics and distributions of RNF6 expression and covariates by vital status. Crude RRs of recurrence associated with RNF6 expression and other predictor variables were first estimated using the univariate Cox proportional hazards regression model. A multivariate Cox model was constructed to estimate the adjusted RR for RNF6 expression. Overall recurrence rate in relation to RNF6 expression was evaluated by the recurrence curve and the log-rank test. A P-value <0.05 was regarded as statistically significant.

Results

High or Up-Regulation of RNF6 in Colon Cancer

RNF6 is Upregulated in Primary Colorectal Tumors

RNF6 mRNA expression was significantly upregulated in 88.9% (8/9) of CRC tumor tissues compared with their adjacent non-tumor tissues (P<0.0001; FIG. 1A). Moreover, RNF6 was readily expressed in 5 of 7 CRC cell lines, but was absent in normal colorectal tissues. The mean protein expression level of RNF6 was significantly higher in primary CRCs compared to their adjacent normal tissues (P<0.01; FIGS. 1, 2A and 2B). These results indicated an aberrant up-regulation of RNF6 in CRC.

Amplification of RNF6 is Associated with Increased Expression of RNF6

Figure 3A:
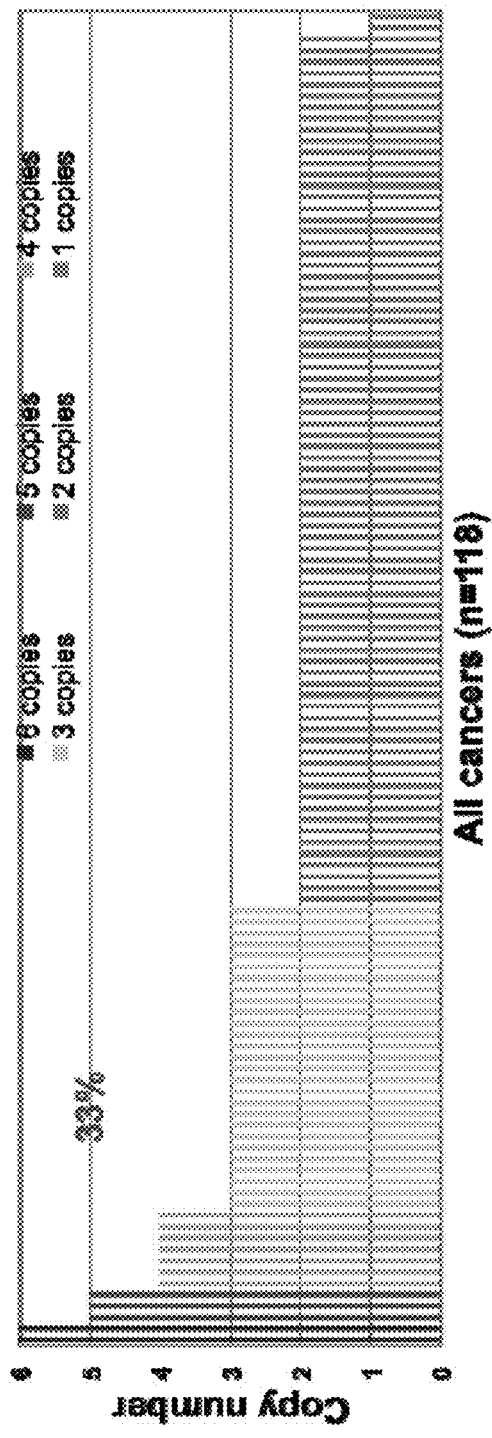
FIGS. 3A and 3B show the correlation of RNF6 copy number variants with its mRNA expression in an embodiment.
Figure 3B:
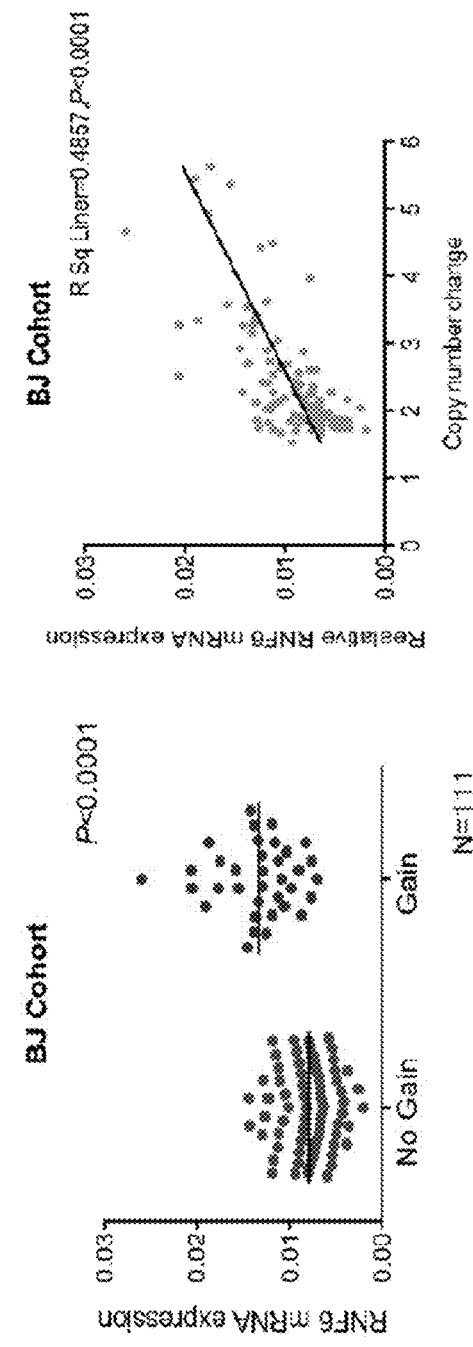

To test whether RNF6 mRNA expression level is correlated with RNF6 copy number variations, the inventors investigated the copy number status of RNF6 in colorectal cancer patients (FIG. 3A). Amplification of RNF6 was detected in 33% (39/118) of primary CRCs. The mRNA expression is higher in copy number gain group compared with no copy number gain group (P<0.0001; FIG. 3B). Moreover, the amplification of RNF6 was positively associated with its mRNA overexpression in the 118 CRC tissues (R sq=0.4857; P<0.0001; FIG. 3B). These results indicated amplification of RNF6 is associated with increased expression of RNF6.

Functional Assay

Promotion of Cancer Proliferation by RNF6

Figure 4B:
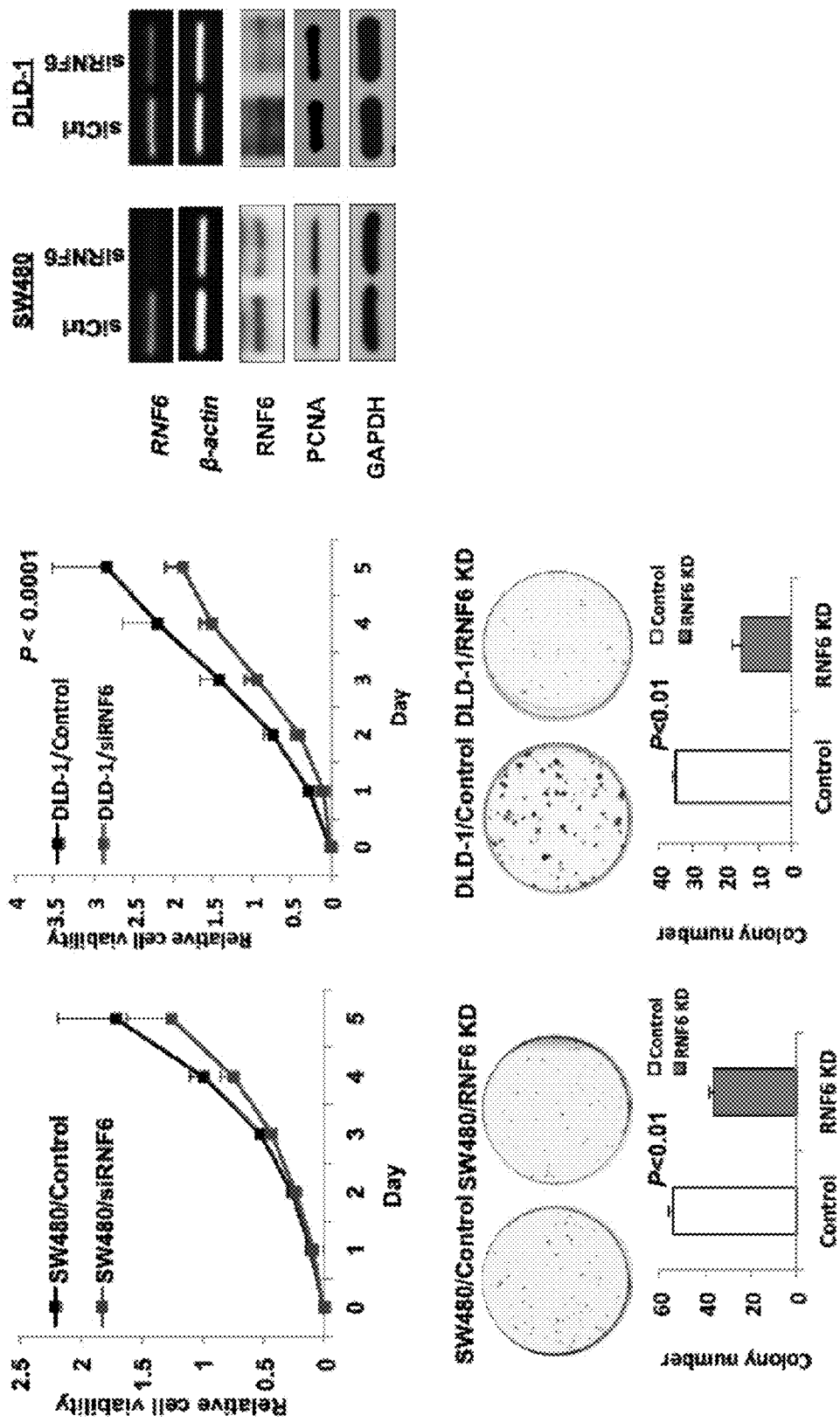

The frequent high expression of RNF6 in CRC cell lines and tissues suggested that RNF6 may have oncogenic function to promote CRC tumorigenesis. To prove this, two stable transfected CRC cell lines (HCT116 and HT29) were generated with RNF6 over-expression. Conversely, the high expression of RNF6 cell lines (SW480 and DLD-1) were used for loss of RNF6-function assay by transit transfection of siRNF6. Effects of RNF6 ectopic expression and knockdown were verified by RT-PCR and Western blot, respectively (FIGS. 4A and 4B). Ectopic expression of RNF6 significantly promote cell viability in HCT116 and HT29 compared to empty vector transfected HCT116 and HT29, while an inverse effect was observed in SW480 and DLD-1 with knockdown of RNF6 (FIG. 4B). In keeping with this, the number of colonies formed in RNF6-transfected HCT116 and HT29 were increased significantly compared to empty vector-transfected HCT116 and HT29, whilst knockdown RNF6 reduced colony formation ability in SW480 and DLD-1 (FIG. 4B). These results indicated that RNF6 was important for promoting CRC cell growth.

To determine the mechanism by which RNF6 promoted cell growth, the effect of RNF6 on cell cycle distribution was analyzed by flow cytometry. Ectopic expression of RNF6 in CRC cells led to a significant decrease in the G1 phase population, and a corresponding promote cell cycle enter S phase and G2 phase (FIG. 5A1). Consistently, RNF6 enhanced the protein expression of the G1-S transition promoter cyclin D1, but reduced G1 gatekeepers $p21^{Cip1}$ and $p27^{Kip1}$. Moreover, p53 causes G2 arrest while RNF6 reduced p53 expression (FIG. 5A2). These results indicated that RNF6 acted on G1/S and G2 checkpoint to promote cell cycle in CRC cells.

Inhibition of Cell Apoptosis by RNF6

To examine the contribution of apoptosis to the observed growth promotion of RNF6-transfected cells, cell apoptosis was determined by flow cytometry with Annexin V-APC and 7-AAD double staining. The result showed a decrease in the numbers of both early apoptotic cells (10.57±0.72% vs 4.84±0.72, P<0.01) and late apoptotic cells (7.26±0.27% vs 4.05±0.33%, P<0.01) in RNF6-transfected HCT116 cells compared to vector-transfected HCT116 cells. Similar effect was observed in RNF6-transfected HT29 cells, which showed an increased cell proportions in both early apoptotic phase (17.77±0.46% vs 12.00±0.95%, P<0.01) and late apoptotic phase (4.28±0.35% vs 2.40±0.22%, P<0.01) compared to the control cells, which was concomitant with enhanced protein expression of pro-apoptotic factors cleaved caspase-8, caspase-9, caspase-3, caspase-7 and PARP. (FIGS. 5B1 and 5B2).

Induction of Cell Migration and Invasion by RNF6

The ectopic expression of RNF6 markedly promoted the cell migration ability in the HCT116 cells and the HT29 cells. Quantitative analyses at 48 h confirmed a significant addition in wound closure in the RNF6-expressing cells compared with the control cells, thereby suggesting that the migration rate of the RNF6-expressing cells was significantly faster than the control cells (FIG. 6A). Matrigel invasion assay also showed that RNF6 significantly induce the invasiveness of HCT116 cells and HT29 cells (FIGS. 6B1 and 6B2). Moreover, the protein expression of the epithelial-mesenchymal transition (EMT) markers, including E-cadherin, N-cadherin and Vimentin in the RNF6-overexpressing cells, were examined by western blot. As shown in FIG. 6C, the ectopic expression of RNF6 reduced the protein levels of E-cadherin, while enhancing N-cadherin and Vimentin in the HCT116 cells and the HT29 cells. Thus, RNF6 promotes the migration and the invasive ability of colon cancer cells by modulating the key EMT regulating factors.

High Expression of RNF6 in Colon Cancer Patients

High Expression of RNF6 is an Independent Predictor of Recurrence in Patients with Colorectal Cancer The association of RNF6 mRNA and clinicopathological features including clinical outcome was analyzed in 160 patients with colorectal cancer. There was no correlation between RNF6 high expression and clinicopathological features such as age, gender, tumor localization, differentiation of CRC patients (Table 3). After adjustment for potential confounding factors including age, gender and TNM stage, high expression of RNF6 was found to predict high recurrence risk of patients with colorectal cancer independently by multivariate Cox regression analysis (RR 1.653, 95% CI 1.016 to 2.690; P=0.043, Tables 4-5). As shown in the Kaplan-Meier survival curves, colorectal cancer patients with high expression of RNF6 had significantly higher recurrence risk than RNF6 low expression group (P=0.0053, log-rank test; FIG. 7).

All patents, patent applications, and other publications, including GenBank Accession Numbers, cited in this application are incorporated by reference in the entirety for all purposes.

TABLE 1

DNA sequences of primers used in this study.

| Primer name | Sequence (5'-3') | |
|---|---|---|
| A) RT-PCR primers for detecting RNF6 mRNA expression : | | |
| RNF6-F | TCAGCCTGACTTGAGAGATGG | SEQ ID NO: 1 |
| RNF6-R | TTCGAGTTGCATTTCCTGTG | SEQ ID NO: 2 |

TABLE 2

Target sequences used in this study

1) SEQ. ID. NO. 3: RNF6 protein coding cDNA sequence (2058 bp)
ATGAATCAGTCTAGATCTGAGATCAGATGGTGGCAGTGAAGAAACCTTACC
TCAAGACCATAATCATCATGAAATGAGAGAAGATGGCAGCAAGAGCGTC
TCCACAGAGAAGAGGCCTATTATCAGTTTATTAATGAACTCAATGATGAA
GATTATCGGCTTATGAGAGACCATAATCTTTTAGGCACCCCTGGAGAAAT
AACATCAGAAGAACTGCAACGCGGTTAGATGGCGTCAAGGAACAACTAG
CATCTCAGCCTGACTTGAGAGATGGAACGAATTACAGAGACTCAGAAGTC
CCTAGAGAAAGTTCACATGAAGATTCTCTTCTAGAATGGTTGAACACCTT
TCGGCGCACAGGAAATGCAACTCGAAGTGGACAAAATGGGAACCAAACTT
GGAGAGCTGTGAGTCGAACAAACCCGAACAATGGAGAGTTTCGGTTTAGT
TTGGAAATCCACGTAAATCATGAAAATAGAGGATTTGAAATTCATGGAGA
AGATTATACAGACATTCCACTTTCAGATAGTAACAGAGATCATACTGCAA
ATAGGCAACAAAGGTCAACTAGTCCTGTGGCTAGGCGAACAAGAAGCCAA
ACCTCAGTGAATTTCAATGGTAGTAGTTCCAACATTCCAAGGACTAGGCT
TGCTTCAAGGGGGCAAAATCCAGCTGAAGGATCTTTCTCAACATTGGGAA
GGTTAAGAAATGGAATTGGGGGAGCAGCTGGCATTCCTCGAGCTAACGCT
TCACGCACTAATTTCAGTAGTCACACAAACCAATCAGGTGGTAGTGAACT
CAGGCAAAGGGAGGGGCAACGGTTTGGAGCAGCACATGTTTGGAAAATG
GGGCTGAAGTAATGTTACAGTGAGGAATACAAACCAAAGATTAGAGCCA
ATAAGATTACGATCTACTTCCAATAGTCGAAGCCGTTCACCAATTCAGAG
ACAGAGTGGCACTGTTTATCATAATTCCCAAAGGGAAAGTAGACCAGTAC
AGCAAACCACTAGAAGATCTGTTAGGAGGAGAGGTAGAACTCGAGTCTTT
TTAGAGCAAGATAGAGAACGAACGCAGAGGTACTGCATATACCCCATT
CTCTAATTCAAGGCTTGTGTCAAGAATAACAGTAGAAGAAGGAGAAGAAT
CCAGCAGATCCTCAACTGCTGTACGACGACATCCAACAATCACACTGGAC
CTTCAAGTGAGAAGGATCCGTCCTGGAGAAAATAGAGATCGGATAGTAT
TGCAAATAGAACTCGATCCAGAGTAGGGCTAGCAGAAAATACAGTCACTA
TTGAAAGCAATAGTGGGGCTTTCGCCGAACCATTTCTCGTTTAGAGCGG
TCAGGTATTCGAACCTATGTTAGTACCATAACAGTTCCTCTTCGTAGGAT
TTCTGAGAATGAGCTTGTTGAGCCATCATCAGTGGCTCTTCGGTCAATTT
TAAGGCAGATCATGACTGGGTTTGGAGAACTGAGTTCTCTAATGGAGGCC
GATTCTGAGTCAGAACTTCAAAGAAATGGCCAGCATTTACCAGACATGCA
CTCAGAACTGAGTAACTTAGGTACAGATAACAACAGGAGCCAGCACAGGG
AAGGTTCCTCTCAAGACAGGCAGGCCCAAGGAGACAGCACTGAAATGCAT
GGTGAAACAGACCACCCAGCCTCATACTCGAAACAGTGACAGTAGGGGG
TGGCAGGCAGTTGCGAAATCCAAACAATTTAGTTGAAACTGGAACACTAC
CCATTCTTCGCCTTGCTCACTTTTTTTTACTAAATGAAAGTGATGATGAT
GATCGAATACGTGGTTTAACCAAAGAGCAGATTGACAATCTTTCCACCAG
GCACTATGAGCATAACAGTATTGATGAACTAGGTGAAAGTCTGTAGTG
TTTGTATTAGTGACTATGTAACTGGAAACAAGCTCAGGCAATTACCTTGC
ATGCATGAATTTCACATTCATTGTATTGACCGATGGCTCTCAGAGAATTG
CACTTGTCCGATCTGTCGGCAGCCTGTTTTAGGGTCAACATAGCAAACA
ATGGGTAA 2) SEQ. ID. NO. 4: RNF6 mRNA sequence (Genbank NM_0059773, 3584 bp)
GCAAGAGGGCGGAACGCGGGACGCCAGGCACCCTAGCTCCCGACGGACGC
AGTTTTCAGTTGCACGGGCGAGCTCCGGGCCGGCTGCGGAGCGACTCCCC
GCCGCCAAGTGGGCGGCGTGGCTGTCGGGAAAGAAGGGCTGGGGCCTGCC
GTTCTTCCTCCCGAGTATCCCCTCCAGCTGGACGACCCCACGCTGCAGCA
CGGGCTTCCGGCTTCTCCTCAGTGGCCAATTCGAGGGCACGCGGCCT
CCGGAGGCGCGGCAAGCCTATCCCGCCTCCCAACCACAGCCTCCAGC
ACCCGAGAGAACGGCCGCCCACAGCACACGTTCTCCGGACAGGAGGGCGA
AGGCCCAAGACCTGGAGAGATGGGCAGCTCTCAAAAAAGGCACAAACAAT
TGAAGGATGGATACATGGCATATGTTAAAAGCGTGTTGAAAGGAAAAATA
AGAAAGCCAGGAATCTCAGGATGAATCAGTCTAGATCGAGATCAGATGGT
GGCAGTGAAGAAACCTTACCTCAAGACCATAATCATCATGAAATGAGAG
AAGATGGCAGCAAGAGCGTCTCCACAGAGAAGAGGCCTATTATCAGTTTA
TTAATGAACTCAATGATGAAGATTATCGGCTTATGAGAGACCATAATCTT
TTAGGCACCCCTGGAGAAATAACATCAGAAGAACTGCAACAGCGGTTAGA
TGGCGTCAAGGAACAACTAGCATCTCAGCCTGACTTGAGAGATGGAACGA
ATTACAGAGACTCAGAAGTCCCTAGAGAAAGTTCACATGAAGATTCTCTT
CTAGAATGGTTGAACACCTTTCGGCGCACAGGAAATGCAACTCGAAGTGG
ACAAAATGGGAACCAAACTTGGAGAGCTGTGAGTCGAACAAACCCGAACA
ATGGAGAGTTTCGGTTTAGTTTGGAAATCCACGTAAATCATGAAAATAGA
GGATTTGAAATTCATGGAGAAGATTATACAGACATTCCACTTTCAGATAG
TAACAGAGATCATACTGCAAATAGGCAACAAAGGTCAACTAGTCCTGTGG
CTAGGCGAACAAGAAGCCAAACCTCAGTGAATTTCAATGGTAGTAGTTCC
AACATTCCAAGGACTAGGCTTGCTTCAAGGGGGCAAAATCCAGCTGAAGG
ATCTTTCTCAACATTGGGAAGGTTAAGAAATGGAATTGGGGGAGCAGCTG
GCATTCCTCGAGCTAACGCTTCACGCACTAATTTCAGTAGTCACACAAAC
CAATCAGGTGGTAGTGAACTCAGGCAAAGGGAGGGGCAACGGTTTGGAGC
AGCACATGTTTGGGAAAATGGGGCTGAAGTAATGTTACAGTGAGGAATA
CAAACCAAAGATTAGAGCCAATAAGATTACGATCTACTTCCAATAGTCGA
AGCCGTTCACCAATTCAGAGACAGAGTGGCACTGTTTATCATAATTCCCA
AAGGGAAAGTAGACCAGTACAGCAAACCACTAGAAGATCTGTTAGGAGGA
GAGGTAGAACTCGAGTCTTTTTAGAGCAAGATAGAGAACGAGAACGCAGA
GGTACTGCATATACCCCATTCTCTAATTCAAGGCTTGTGTCAAGAATAAC
AGTAGAAGAAGGAGAAGAATCCAGCAGATCCTCAACTGCTGTACGACGAC
ATCCAACAATCACACTGGACCTTCAAGTGAGAAGGATCCGTCCTGGAGAA
AATAGAGATCGGGATAGTATTGCAAATAGAACTCGATCCAGAGTAGGGCT
AGCAGAAAATACAGTCACTATTGAAAGCAATAGTGGGGCTTTCGCCGAA
CCATTTCTCGTTTAGAGCGGTCAGGTATTCGAACCTATGTTAGTACCATA
ACAGTTCCTCTTCGTAGGATTTCTGAGAATGAGCTTGTTGAGCCATCATC
AGTGGCTCTTCGGTCAATTTTAAGGCAGATCATGACTGGGTTTGGAGAAC
TGAGTTCTCTAATGGAGGCCGATTCTGAGTCAGAACTTCAAAGAAATGGC
CAGCATTTACCAGACATGCACTCAGAACTGAGTAACTTAGGTACAGATAA
CAACAGGAGCCAGCACAGGGAAGGTTCCTCTCAAGACAGGCAGGCCCAAG
GAGACAGCACTGAAATGCATGGTGAAACAGAGACCACCCAGCCTCATACT
CGAAACAGTGACAGTAGGGGTGGCAGGCAGTTGCGAAATCCAAACAATTT
AGTTGAAACTGGAACACTACCCATTCTTCGCCTTGCTCACTTTTTTTTAC
TAAATGAAAGTGATGATGATGATGATCGAATAGCTGGTTTAACCAAAGACAG
ATTGACAATCTTTCCACCAGGCACTATGAGCATAACAGTATTGATAGTGA
ACTAGGTAAATCTGTAGTGTTTGTATTAGTGACTATGTAACTGGAAACA
AGCTCAGGCAATTACCTTGCATGCATGAATTTCACATTCATTGTATTGAC
CGATGGCTCTCAGAGACAGTGTCCGATCTGTCGGCAGCCTGTTTT
AGGGTCTAACATAGCAAACAATGGGTAAGGTGATGGATCTACTCAAATA
CTGTTTTTTAGTGAACTGAATGTTCAAGCATTGTTTTGCTGAGTTATTT
GTGATTAGCTAACCAGGATGAAAAATAACAGATTATATATAGTTTGAACT
ATTTTTCGTGTGCTTTTTAACTTTGTTAAAAAGAAATTTATATAAAATT
TAAAATACAAATGTTAAATTATCCAGAAATACAGAATAGTTAATATTGCT
AGAACCAAATAACCTCTAAATGTTTTTATTTTGGTAATTTTGTCATGCT
AAGCACTTTTGTATCTGCACAATTCAGTAGGTTAAGAATCAATCTTCTTT
TTCTTAATAGTACAGCAGACTTTAGCTTCAAGTTTCATAGGCTTAGTACT
TATATCTAGACATTTGTGTCTAAATAAGCTTTTCATTAACTTTTATTTT
AAGGACAGTATCTTTTCATGAAAGAGTATTTGGCTGAATGTTTGCTATAT
ATATGTTACTTGAAATGTTAAATTTAATATGCAGCATACCATAGGTGTAT
ATATAGGTATATAATTTTAAGGTTAAAATATTCAGTCTACAAGTTTGTTT
CTTATTTAAGCTTTTGGGCTAATACTGCATATGGCACAATGTTTAATATT
GGCAAGTTCATCTCAGAGAAAGGGGATTCAGATATAATTTTAAAGTAGAG
ATAATTTACTGAAGCGTCTCTGACAATCTAACTTATTAGACAGCAAGCAA
TATATAATACTGAAAAAGTATTCAGAAATGGAAAATTTACATCATATAGG
TTATTTAACTTGTGTTCAGCCTTTTTGTAACTTTTTTGAAAGTGCAAACA
ATTCTTTGGATTATTAAATAAGGTATACAGTATGCATGGTTTCTCAAATT
TAGTTTTAAAATCTAAAAGTCTATAAAGAATCAGATGCATAGGCAATATG
TTAAGTTCACTTGGAGGCTAAAAATCTCCAGTGAAAACAAAACGAAAACC
TTTAAGAGAATGTAGAGTTTATATAAACACAAAGTATGCATTGAAGATCT
GTTTCTACCAATAAACATTAAAACAAAGACTGTA 3) SEQ. ID. NO. 5: Partial coding sequence used to detect human RNF6 mRNA (81 bp).
AACGAATTACAGAGACTCAGAAGTCCCTAGAGAAAGTTCACATGAAGATT
CTCTTCTAGAATGGTTGAACACCTTTCGGCG 4) SEQ. ID. NO. 6: RNF6 protein sequence, 685 amino acids
MNQSRSRSDGGSEETLPQDHNHHENERRWQQERLHREEAYYQFINELNDE
DYRLMRDHNLLGTPGEITSEELQQRLDGVKEQLASQPDLRDGTNYRDSEV
PRESSHEDSLLEWLNTFRRTGNATRSGQNGNQTWRAVSRTNPNNGEFRFS
LEIHVNHENRGFEIHGEDYTDIPLSDSNRDHTANRQQRSTSPVARRTRSQ
TSVNFNGSSSNIPRTRLASRGQNPAEGSFSTLGRLRNGIGGAAGIPRANA
SRTNFSSHTNQSGGSELRQREGQRFGAAHVWENGARSNVTVRNTNQRLEP
IRLRSTSNSRSRSPIQRQSGTVYHNSQRESRPVQQTTRRSVRRRGRTRVF
LEQDRERERRGTAYTPFSNSRLVSRITVEEGEESSRSSTAVRRHPTITLD
LQVRRIRPGENRDRDSIANRTRSRVGLAENTVTIESNSGGFRRTISRLER
SGIRTYVSTITVPLRRISENELVEPSSVALRSILRQIMTGFGELSSLMEA
DSESELQRNGQHLPDMHSELSNLGTDNNRSQHREGSSQDRQAQGDSTEMH
GENETTQPHTRNSDSRGGRQLRNPNNLVETGTLPILRLAHFFLLNESDDD
DRIRGLTKEQIDNLSTRHYEHNSIDSELGKICSVCISDYVTGNKLRQLPC
MHEFHIHCIDRWLSENCTCPICRQPVLGSNIANNG

TABLE 3

Clinicopathological characteristics and RNF6 expression in tumor tissues of colorectal cancer patients

| Variable | High(n = 78) | % | Low(n = 82) | % | P value |
|---|---|---|---|---|---|
| Age ( y ± SD) | 60.65 ± 13.15 | | 61.16 ± 14.18 | | 0.814 |
| Gender | | | | | 0.743 |
| M | 51 | 65.38 | 51 | 62.20 | |
| F | 27 | 34.62 | 31 | 37.80 | |
| Localization | | | | | 0.181 |

TABLE 3-continued

Clinicopathological characteristics and RNF6 expression in tumor tissues of colorectal cancer patients

| Variable | High(n = 78) | % | Low(n = 82) | % | P value |
|---|---|---|---|---|---|
| Colon | 22 | 28.12 | 32 | 39.02 | |
| Rectum | 56 | 71.79 | 50 | 60.98 | |
| Differentiation | | | | | 0.083 |
| Low | 8 | 10.26 | 17 | 20.73 | |
| high | 70 | 89.74 | 65 | 79.27 | |
| TNM | | | | | 0.004 |
| I/II | 24 | 30.76 | 44 | 53.66 | |
| III | 54 | 69.23 | 38 | 46.34 | |

NOTE:
SD, standard deviation

TABLE 4

Univariate Cox regression analysis of potential recurrence predictors for Colorectal Cancer patients

| Variable | RR (95% CI) | p-value |
|---|---|---|
| Age | 1.148(0.720 to 1.832) | 0.561 |
| Gender | | |
| Female | 0.756(0.457 to 1.250) | 0.276 |
| Male | 1.00 | |
| Localization | | |
| Rectum | 0.960(0.552 to 1.485) | 0.694 |
| Colon | 1.00 | |
| Differentiation | | |
| Low | 1.258(0.675 to 2.346) | 0.470 |
| Moderate/High | 1.00 | |
| TNM stage | | |
| I/II | 0.399(0.237 to 0.672) | 0.001 |
| III | 1.00 | |
| RNF6 | | |
| High | 1.947(1.208 to 3.140) | 0.006 |
| Low | 1.00 | |

TABLE 5

Multivariate Cox regression analysis of potential recurrence predictors for Colorectal Cancer patients

| Variable | RR (95% CI) | p-value |
|---|---|---|
| Age | 0.997(0.618 to 1.607) | 0.989 |
| Gender | | |
| Female | 0.802(0.480 to 1.341) | 0.401 |
| Male | 1.00 | |
| TNM stage | | |
| I/II | 0.452(0.265 to 0.711) | 0.004 |
| III | 1.00 | |
| RNF6 | | |
| High | 1.653(1.016 to 2.690) | 0.043 |
| Low | 1.00 | |

LIST OF REFERENCES

1. Macdonald D H, Lahiri D, Sampath A, Chase A, Sohal J, Cross N C. (1999) Cloning and characterization of RNF6, a novel RING finger gene mapping to 13q12.Genomics. 15; 58(1):94-7.
2. Xu K, Shimelis H, Linn D E, Jiang R, Yang X, Sun F, Guo Z, Chen H, Li W, Chen H, Kong X, Melamed J, Fang S, Xiao Z, Veenstra T D, Qiu Y. (2009) Regulation of androgen receptor transcriptional activity and specificity by RNF6-induced ubiquitination. Cancer Cell. 15(4):270-282.
3. Tursun B, Schlüter A, Peters M A, Viehweger B, Ostendorff H P, Soosairajah J, Drung A, Bossenz M, Johnsen S A, Schweizer M, Bernard O, Bach I. (2005) The ubiquitin ligase Rnf6 regulates local LIM kinase 1 levels in axonal growth cones. *Genes Dev.* 19(19):2307-2319.
4. Linn D E, Yang X, Xie Y, Alfano A, Deshmukh D, Wang X, Shimelis H, Chen H, Li W, Xu K, Chen M, Qiu Y. (2012) Differential regulation of androgen receptor by PIM-1 kinases via phosphorylation-dependent recruitment of distinct ubiquitin E3 ligases. *J Biol Chem.* 287 (27):22959-22968.
5. Lopez P, Vidal F, Martin L, Lopez-Fernandez L A, Rual J F, Rosen B S, Cuzin F, Rassoulzadegan M. (2002) Gene control in germinal differentiation: RNF6, a transcription regulatory protein in the mouse sertoli cell. Mol Cell Biol. 22(10):3488-3496.
6. Lo H S, Hu N, Gere S, Lu N, Su H, Goldstein A M, Taylor P R, Lee M P. (2002) Identification of somatic mutations of the RNF6 gene in human esophageal squamous cell carcinoma. Cancer Res. 62(15):4191-4193.

What is claimed is:

1. A method for assessing risk for colon cancer, comprising the steps of:
   (a) performing a polymerase chain reaction (PCR) to determine RNF6 level in a colon tissue sample taken from a human subject, wherein the RNF6 level is genomic RNF6 level or RNF6 mRNA level, and wherein a primer comprising the nucleotide sequence of SEQ ID NO:1 or 2 is used in the PCR;
   (b) comparing the RNF6 level obtained in step (a) with a standard control level obtained from a non-cancer colon tissue sample; and
   (c) determining the subject, who has an increased RNF6 level compared with the standard control level, as having an increased risk for colon cancer.

2. The method of claim 1, wherein the colon tissue sample is a colon mucosa sample.

3. The method of claim 1, wherein the RNF6 level is genomic RNF6 DNA level.

4. The method of claim 1, wherein the RNF6 level is RNF6 mRNA level and the PCR is a reverse transcriptase-PCR (RT-PCR).

5. The method of claim 1, wherein a first primer comprising the nucleotide sequence of SEQ ID NO:1 and a second primer comprising the nucleotide sequence of SEQ ID NO:2 are used in the PCR.

6. The method of claim 1, when the subject is indicated as having an increased risk for colon cancer, further comprising repeating step (a) at a later time using the sample type of sample from the subject, wherein an increase in the RNF6 level at the later time as compared to the amount from the original step (a) indicates a heightened risk of colon cancer, and a decrease indicates a lessened risk for colon cancer.

7. The method of claim 1, comprising the steps of:
   (a) performing a PCR to measure RNF6 level in a colon cancer sample taken from a first human colon cancer patient, wherein the RNF6 level is genomic RNF6 DNA level or RNF6 mRNA level, and wherein a first primer comprising the nucleotide sequence of SEQ ID NO:1 or 2 is used in the PCR,
   (b) comparing the RNF6 level obtained in step (a) with RNF6 level from another colon cancer sample of the same type obtained from a second human colon cancer patient and measured by step (a), and (c) determining the first human colon cancer patient, who has a higher RNF6 level compared with the RNF6 level determined in the other colon cancer sample of the same type obtained from a second human colon cancer patient and measured by step (a), as having an increased risk for recurrence of colon cancer compared with the second human colon cancer patient.

8. The method of claim 7, wherein the colon cancer sample is a colon mucosa sample.

9. The method of claim 7, wherein the RNF6 level is genomic RNF6 DNA level.

10. The method of claim 7, wherein the RNF6 level is RNF6 mRNA level and the PCR is a reverse transcriptase-PCR (RT-PCR).

11. The method of claim 7, wherein the first human colon cancer patient has previously received treatment for colon cancer.

12. The method of claim 7, wherein the second human colon cancer patient has an RNF6 level essentially the same as the RNF6 level determined in another colon tissue sample of the same type that is (1) obtained from a healthy individual who does not have colon cancer or an elevated risk for developing colon cancer; and (2) measured by step (a).

13. The method of claim 7, wherein a first primer comprising the nucleotide sequence of SEQ ID NO:1 and a second primer comprising the nucleotide sequence of SEQ ID NO:2 are used in the PCR.

\* \* \* \* \*

UNITED STATES PATENT AND TRADEMARK OFFICE
CERTIFICATE OF CORRECTION

| | |
|---|---|
| PATENT NO. | : 10,457,993 B2 |
| APPLICATION NO. | : 15/085790 |
| DATED | : October 29, 2019 |
| INVENTOR(S) | : Jun Yu and Joseph Jao Yiu Sung |

It is certified that error appears in the above-identified patent and that said Letters Patent is hereby corrected as shown below:

On the Title Page

(56) References Cited, Column 2, Line 8 please correct the Lo et al citation to read as follows:
LO et al., "Identification of Somatic Mutations of the RNF6 in Human Esophageal Squamous Cell Carcinoma," Cancer Research 62, 4191-4193, August 1, 2002.

Signed and Sealed this
Twenty-fifth Day of February, 2020

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: synthetic forward primer

<400> SEQUENCE: 1
tcagcctgac ttgagagatg g                                         21
```

```
<210> SEQ ID NO 2
<211> LENGTH: 20
<212> TYPE: DNA
<213> ORGANISM: Artificial Sequence
<220> FEATURE:
<223> OTHER INFORMATION: synthetic forward reverse

<400> SEQUENCE: 2
ttcgagttgc atttcctgtg                                                20

<210> SEQ ID NO 3
<211> LENGTH: 2058
<212> TYPE: DNA
<213> ORGANISM: Homo sapiens

<400> SEQUENCE: 3
atgaatcagt ctagatcgag atcagatggt ggcagtgaag aaaccttacc tcaagaccat      60
aatcatcatg aaaatgagag aagatggcag caagagcgtc tccacagaga agaggcctat     120
tatcagttta ttaatgaact caatgatgaa gattatcggc ttatgagaga ccataatctt     180
ttaggcaccc ctggagaaat aacatcagaa gaactgcaac agcggttaga tggcgtcaag     240
gaacaactag catctcagcc tgacttgaga gatggaacga attacagaga ctcagaagtc     300
cctagagaaa gttcacatga agattctctt ctagaatggt tgaacaccct tcggcgcaca     360
ggaaatgcaa ctcgaagtgg acaaaatggg aaccaaactt ggagagctgt gagtcgaaca     420
aacccgaaca atggagagtt tcggtttagt ttggaaatcc acgtaaatca tgaaaataga     480
ggatttgaaa ttcatggaga agattataca gacattccac tttcagatag taacagagat     540
catactgcaa ataggcaaca aaggtcaact agtcctgtgg ctaggcgaac aagaagccaa     600
acctcagtga atttcaatgg tagtagttcc aacattccaa ggactaggct tgcttcaagg     660
gggcaaaatc cagctgaagg atctttctca acattgggaa ggttaagaaa tggaattggg     720
ggagcagctg gcattcctcg agctaacgct tcacgcacta atttcagtag tcacacaaac     780
caatcaggtg gtagtgaact caggcaaagg gaggggcaac ggtttggagc agcacatgtt     840
tgggaaaatg gggctagaag taatgttaca gtgaggaata caaaccaaag attagagcca     900
ataagattac gatctacttc caatagtcga agccgttcac caattcagag acagagtggc     960
actgtttatc ataattccca aagggaaagt agaccagtac agcaaaccac tagaagatct    1020
gttaggagga gaggtagaac tcgagtcttt ttagagcaag atagagaacg agaacgcaga    1080
ggtactgcat atacccccatt ctctaattca aggcttgtgt caagaataac agtagaagaa    1140
ggagaagaat ccagcagatc ctcaactgct gtacgacgca atccaacaat cacactggac    1200
cttcaagtga aaggatccg tcctggagaa aatagagatc gggatagtat tgcaaataga    1260
actcgatcca gagtagggct agcagaaaat acagtcacta ttgaaagcaa tagtgggggc    1320
tttcgccgaa ccatttctcg tttagagcgg tcaggtattc gaacctatgt tagtaccata    1380
acagttcctc ttcgtaggat ttctgagaat gagcttgttg agccatcatc agtggctctt    1440
cggtcaattt taaggcagat catgactggg tttggagaac tgagttctct aatggaggcc    1500
gattctgagt cagaacttca aagaaatggc cagcatttac cagacatgca ctcagaactg    1560
agtaacttag gtacagataa caacaggagc cagcacaggg aaggttcctc tcaagacagg    1620
caggcccaag gagacagcac tgaaatgcat ggtgaaaacg agaccaccca gcctcatact    1680
cgaaacagtg acagtagggg tggcaggcag ttgcgaaatc aaacaatttt agttgaaact    1740
ggaacactac ccattcttcg ccttgctcac ttttttttac taaatgaaag tgatgatgat    1800
```

```
gatcgaatac gtggtttaac caaagagcag attgacaatc tttccaccag gcactatgag      1860
cataacagta ttgatagtga actaggtaaa atctgtagtg tttgtattag tgactatgta      1920
actggaaaca agctcaggca attaccttgc atgcatgaat ttcacattca ttgtattgac      1980
cgatggctct cagagaattg cacttgtccg atctgtcggc agcctgtttt agggtctaac      2040
atagcaaaca atgggtaa                                                    2058

<210> SEQ ID NO 4
<211> LENGTH: 3584
<212> TYPE: DNA
<213> ORGANISM: Homo sapiens

<400> SEQUENCE: 4
gcaagagggc ggaacgcggg acgccaggca ccctagctcc cgacggacgc agttttcagt        60
tgcacgggcg agctccgggc cggctgcgga gcgactcccc gccgccaagt gggcggcgtg       120
gctgtcggga aagaagggct ggggcctgcc gttcttcctc ccgagtatcc cctccagctg       180
gacgacccca cgctgcagca cgggcttccg gcttctctcc tcagtggcca attcgagggc       240
acagcgggct ccggaggcgc ggcggcaagc ctatcccgcc tcccaaccac agcctccagc       300
acccgagaga acgccgccc acagcacacg ttctccggac aggagggcga aggcccaaga       360
cctggagaga tggcagctc tcaaaaaagg cacaaacaat tgaaggatgg ataccatggc       420
atatgttaaa agcgtgttga aaggaaaata agaaagccag gaatctcagg atgaatcagt       480
ctagatcgag atcagatggt ggcagtgaag aaaccttacc tcaagaccat aatcatcatg       540
aaaatgagag aagatggcag caagagcgtc tccacagaga agaggcctat tatcagttta       600
ttaatgaact caatgatgaa gattatcggc ttatgagaga ccataatctt ttaggcaccc       660
ctggagaaat aacatcagaa gaactgcaac agcggttaga tggcgtcaag gaacaactag       720
catctcagcc tgacttgaga gatggaacga attacagaga ctcagaagtc cctagagaaa       780
gttcacatga agattctctt ctagaatggt tgaacacctt tcggcgcaca ggaaatgcaa       840
ctcgaagtgg acaaaatggg aaccaaactt ggagagctgt gagtcgaaca aacccgaaca       900
atggagagtt tcggtttagt ttggaaatcc acgtaaatca tgaaaataga ggatttgaaa       960
ttcatggaga agattataca gacattccac tttcagatag taacagagat catactgcaa      1020
ataggcaaca aaggtcaact agtcctgtgg ctaggcgaac aagaagccaa acctcagtga      1080
atttcaatgg tagtagttcc aacattccaa ggactaggct tgcttcaagg gggcaaaatc      1140
cagctgaagg atctttctca acattgggaa ggttaagaaa tggaattggg ggagcagctg      1200
gcattcctcg agctaacgct tcacgcacta atttcagtag tcacacaaac caatcaggtg      1260
gtagtgaact caggcaaagg gaggggcaac ggtttggagc agcacatgtt tgggaaaatg      1320
gggctagaag taatgttaca gtgaggaata caaaccaaag attagagcca ataagattac      1380
gatctacttc caatagtcga agccgttcac caattcagag acagagtggc actgtttatc      1440
ataattccca aagggaaagt agaccagtac agcaaaccac tagaagatct gttaggagga      1500
gaggtagaac tcgagtcttt ttagagcaag atagagaacg agaacgcaga ggtactgcat      1560
atacccattt tctctaattca aggcttgtgt caagaataac agtagaagaa ggagaagaat      1620
ccagcagatc ctcaactgct gtacgacgac atccaacaat cacactggac cttcaagtga      1680
gaaggatccg tcctggagaa aatagagatc gggatagtat tgcaaataga actcgatcca      1740
gagtagggct agcagaaaat acagtcacta ttgaaagcaa tagtggggc tttgccgaa       1800 ccatttctcg tttagagcgg tcaggtattc gaacctatgt tagtaccata acagttcctc      1860
```

```
ttcgtaggat ttctgagaat gagcttgttg agccatcatc agtggctctt cggtcaattt      1920
taaggcagat catgactggg tttgagaac tgagttctct aatggaggcc gattctgagt      1980
cagaacttca agaaatggc cagcatttac cagacatgca ctcagaactg agtaacttag      2040
gtacagataa caacaggagc cagcacaggg aaggttcctc tcaagacagg caggcccaag      2100
gagacagcac tgaaatgcat ggtgaaaacg agaccaccca gcctcatact cgaaacagtg      2160
acagtagggg tggcaggcag ttgcgaaatc caaacaattt agttgaaact ggaacactac      2220
ccattcttcg ccttgctcac tttttttac taaatgaaag tgatgatgat gatcgaatac       2280
gtggtttaac caaagagcag attgacaatc tttccaccag gcactatgag cataacagta      2340
ttgatagtga actaggtaaa atctgtagtg tttgtattag tgactatgta actggaaaca      2400
agctcaggca attccttgc atgcatgaat ttcacattca ttgtattgac cgatggctct       2460
cagagaattg cacttgtccg atctgtcggc agcctgtttt agggtctaac atagcaaaca      2520
atgggtaagg tgatgggatc tactcaaata ctgttttta gtagaactga atgttcaagc       2580
attgttttgc tgagttattt gtgattagct aaccaggatg aaaaataaca gattatatat      2640
agtttgaact atttttcgtg tgctttttta aacttgttaa aaagaaattt atataaaatt      2700
taaaatacaa atgttaaatt atccagaaat acagaatagt taatattgct agaaccaaat      2760
aacctctaaa atgtttttat tttggtaatt ttgtcatgct aagcactttt gtatctgcac      2820
aattcagtag gttaagaatc aatcttcttt ttcttaatag tacagcagac tttagcttca      2880
agtttcatag gcttagtact tatatctaga catttgtgtc taaataagct tttcattaac      2940
tttttatttt aaggacagta tcttttcatg aaagagtatt tggctgaatg tttgctatat      3000
atatgttact tgaaatgtta aatttaatat gcagcatacc ataggtgtat atataggtat      3060 ataatttaa ggttaaaata ttcagtctac aagtttggtt cttatttaag cttttgggct       3120
aatactgcat atggcacaat gtttaatatt ggcaagttca tctcagagaa aggggattca      3180
gatataattt taaagtagag ataatttact gaagcgtctc tgacaatcta acttattaga      3240
cagcaagcaa tatataatac tgaaaaagta ttcagaaatg gaaaatttac atcatatagg      3300
ttatttaact tgtgttcagc cttttttgtaa ctttttttgaa agtgcaaaca attctttgga    3360
ttattaaata aggtatacag tatgcatggt ttctcaaatt tagttttaaa atctaaaagt      3420
ctataaagaa tcagatgcat aggcaatatg ttaagttcac ttggaggcta aaaatctcca     3480
gtgaaaacaa aacgaaaacc tttaagagaa tgtagagttt atataaacac aaagtatgca      3540
ttgaagatct gtttctacca ataaacatta aacaaagac tgta                        3584
```

<210> SEQ ID NO 5
<211> LENGTH: 81
<212> TYPE: DNA
<213> ORGANISM: Artificial Sequence
<220> FEATURE:
<223> OTHER INFORMATION: synthetic coding sequence

<400> SEQUENCE: 5

```
aacgaattac agagactcag aagtccctag agaaagttca catgaagatt ctcttctaga      60
atggttgaac cctttcggc g                                                 81
```

<210> SEQ ID NO 6
<211> LENGTH: 685
<212> TYPE: PRT
<213> ORGANISM: Homo sapiens

<400> SEQUENCE: 6

```
Met Asn Gln Ser Arg Ser Arg Ser Asp Gly Gly Ser Glu Glu Thr Leu
1               5                   10                  15

Pro Gln Asp His Asn His His Glu Asn Glu Arg Arg Trp Gln Gln Glu
            20                  25                  30

Arg Leu His Arg Glu Glu Ala Tyr Tyr Gln Phe Ile Asn Glu Leu Asn
        35                  40                  45

Asp Glu Asp Tyr Arg Leu Met Arg Asp His Asn Leu Leu Gly Thr Pro
    50                  55                  60

Gly Glu Ile Thr Ser Glu Glu Leu Gln Gln Arg Leu Asp Gly Val Lys
65                  70                  75                  80

Glu Gln Leu Ala Ser Gln Pro Asp Leu Arg Asp Gly Thr Asn Tyr Arg
                85                  90                  95

Asp Ser Glu Val Pro Arg Glu Ser Ser His Glu Asp Ser Leu Leu Glu
            100                 105                 110

Trp Leu Asn Thr Phe Arg Arg Thr Gly Asn Ala Thr Arg Ser Gly Gln
        115                 120                 125

Asn Gly Asn Gln Thr Trp Arg Ala Val Ser Arg Thr Asn Pro Asn Asn
130                 135                 140

Gly Glu Phe Arg Phe Ser Leu Glu Ile His Val Asn His Glu Asn Arg
145                 150                 155                 160

Gly Phe Glu Ile His Gly Glu Asp Tyr Thr Asp Ile Pro Leu Ser Asp
                165                 170                 175

Ser Asn Arg Asp His Thr Ala Asn Arg Gln Gln Arg Ser Thr Ser Pro
            180                 185                 190

Val Ala Arg Arg Thr Arg Ser Gln Thr Ser Val Asn Phe Asn Gly Ser
        195                 200                 205

Ser Ser Asn Ile Pro Arg Thr Arg Leu Ala Ser Arg Gly Gln Asn Pro
210                 215                 220

Ala Glu Gly Ser Phe Ser Thr Leu Gly Arg Leu Arg Asn Gly Ile Gly
225                 230                 235                 240

Gly Ala Ala Gly Ile Pro Arg Ala Asn Ala Ser Arg Thr Asn Phe Ser
                245                 250                 255

Ser His Thr Asn Gln Ser Gly Gly Ser Glu Leu Arg Gln Arg Glu Gly
            260                 265                 270

Gln Arg Phe Gly Ala Ala His Val Trp Glu Asn Gly Ala Arg Ser Asn
        275                 280                 285

Val Thr Val Arg Asn Thr Asn Gln Arg Leu Glu Pro Ile Arg Leu Arg
290                 295                 300

Ser Thr Ser Asn Ser Arg Ser Arg Ser Pro Ile Gln Arg Gln Ser Gly
305                 310                 315                 320

Thr Val Tyr His Asn Ser Gln Arg Glu Ser Arg Pro Val Gln Gln Thr
                325                 330                 335

Thr Arg Arg Ser Val Arg Arg Arg Gly Arg Thr Arg Val Phe Leu Glu
            340                 345                 350

Gln Asp Arg Glu Arg Glu Arg Arg Gly Thr Ala Tyr Thr Pro Phe Ser
        355                 360                 365

Asn Ser Arg Leu Val Ser Arg Ile Thr Val Glu Glu Gly Glu Ser
370                 375                 380

Ser Arg Ser Ser Thr Ala Val Arg Arg His Pro Thr Ile Thr Leu Asp
385                 390                 395                 400

Leu Gln Val Arg Arg Ile Arg Pro Gly Glu Asn Arg Asp Arg Asp Ser
                405                 410                 415
```

-continued

```
Ile Ala Asn Arg Thr Arg Ser Arg Val Gly Leu Ala Glu Asn Thr Val
            420                 425                 430

Thr Ile Glu Ser Asn Ser Gly Gly Phe Arg Arg Thr Ile Ser Arg Leu
        435                 440                 445

Glu Arg Ser Gly Ile Arg Thr Tyr Val Ser Thr Ile Thr Val Pro Leu
    450                 455                 460

Arg Arg Ile Ser Glu Asn Glu Leu Val Glu Pro Ser Ser Val Ala Leu
465                 470                 475                 480

Arg Ser Ile Leu Arg Gln Ile Met Thr Gly Phe Gly Glu Leu Ser Ser
                485                 490                 495

Leu Met Glu Ala Asp Ser Glu Ser Glu Leu Gln Arg Asn Gly Gln His
            500                 505                 510

Leu Pro Asp Met His Ser Glu Leu Ser Asn Leu Gly Thr Asp Asn Asn
        515                 520                 525

Arg Ser Gln His Arg Glu Gly Ser Ser Gln Asp Arg Gln Ala Gln Gly
    530                 535                 540

Asp Ser Thr Glu Met His Gly Glu Asn Glu Thr Thr Gln Pro His Thr
545                 550                 555                 560

Arg Asn Ser Asp Ser Arg Gly Gly Arg Gln Leu Arg Asn Pro Asn Asn
                565                 570                 575

Leu Val Glu Thr Gly Thr Leu Pro Ile Leu Arg Leu Ala His Phe Phe
            580                 585                 590

Leu Leu Asn Glu Ser Asp Asp Asp Arg Ile Arg Gly Leu Thr Lys
                595                 600                 605

Glu Gln Ile Asp Asn Leu Ser Thr Arg His Tyr Glu His Asn Ser Ile
    610                 615                 620

Asp Ser Glu Leu Gly Lys Ile Cys Ser Val Cys Ile Ser Asp Tyr Val
625                 630                 635                 640

Thr Gly Asn Lys Leu Arg Gln Leu Pro Cys Met His Glu Phe His Ile
                645                 650                 655

His Cys Ile Asp Arg Trp Leu Ser Glu Asn Cys Thr Cys Pro Ile Cys
                660                 665                 670

Arg Gln Pro Val Leu Gly Ser Asn Ile Ala Asn Asn Gly
            675                 680                 685
```